US007125964B2

(12) United States Patent
Luxembourg et al.

(10) Patent No.: US 7,125,964 B2
(45) Date of Patent: Oct. 24, 2006

(54) PURIFICATION OF ANTIGEN-SPECIFIC T CELLS

(75) Inventors: Alain T. Luxembourg, LaJolla, CA (US); Michael R. Jackson, Del Mar, CA (US); Per A. Peterson, Sante Fe, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/785,472

(22) Filed: Feb. 23, 2004

(65) Prior Publication Data

US 2004/0137617 A1    Jul. 15, 2004

Related U.S. Application Data

(60) Continuation of application No. 09/434,965, filed on Nov. 5, 1999, now abandoned, which is a division of application No. 08/909,549, filed on Aug. 12, 1997, now abandoned.

(60) Provisional application No. 60/025,588, filed on Sep. 6, 1996.

(51) Int. Cl.
*C07K 14/74* (2006.01)
(52) U.S. Cl. ..................... 530/403; 530/395
(58) Field of Classification Search ............... 530/395, 530/403
See application file for complete search history.

(56) References Cited

U.S. PATENT DOCUMENTS

| | | | |
|---|---|---|---|
| 5,045,320 | A | 9/1991 | Mescher |
| 5,521,288 | A | 5/1996 | Linsley et al. |
| 5,529,921 | A | 6/1996 | Peterson et al. |
| 5,583,031 | A | 12/1996 | Stern |
| 5,595,881 | A | 1/1997 | Kendrick et al. |
| 5,731,160 | A | 3/1998 | Melief et al. |
| 5,827,737 | A | 10/1998 | Peterson et al. |

FOREIGN PATENT DOCUMENTS

| | | |
|---|---|---|
| CA | 2 069 541 | 11/1993 |
| EP | 0 814 838 | 1/1998 |
| WO | WO 96/05287 | 2/1996 |
| WO | WO 96/27392 | 9/1996 |

OTHER PUBLICATIONS

Burshtyn, DN et al. (1993)Journal of Immunology. 151:3070-3080.*
Nikolic-Zugic, J et al. (1990) Eur. J. Immunol. 20:2431-2437.*
Boyd, LF et al. (1992) Proc. Nat. Acad. Sci. (USA). 89:2242-2246.*
Chang, KW et al. J. Biotech. [2005] 116:359-367.*
Agrawal, G.B. et al., "Mathematical Modeling of Helper T Lymphocyte/Antigen-Presenting Cell Interactions: Analysis of Methods for Modifying Antigen Processing and Presentation", *J. Theor. Biol*, 1996, 182, 487-504.

Ashman, R.F., "Lymphocyte Receptor Movement Induced by Sheep Erythrocyte Binding", *J. Immunol.*, 1973, 111, 212-220.
Altman, J.D., et al., "Phenotypic Analysis of Antigen-Specific T Lymphocytes", *Science*, 1996, 274, 94-96.
Bellone, G. et al., "Regulatory Action of Prolactin on the In Vitro Growth of CD34+ Ve Human Hemopoietic Progenitor Cells", *J. Cell Physiol.*, 1995, 163, 221-231.
Borrow, P. et al., "Lymphocytic Choriomeningitis Virus", *Viral Pathogenesis*, 1997, 593-627.
Brinkman, et al., "TCR-Independent Activation of Human CD4+45RO T Cells by Anti-CD38 Plus IL-2; Induction of Clonal Expansion and Priming for a Th2 Phenotype", *The Journal of Immunology*, Jun. 1, 1996, 156, 4100-4106.
Cai, Z. et al., "Influence of Antigen Dose and Costimulation on the Primary Response of CD8+ I Cells in Vitro", *J. Exp. Med.*, 1996, 183, 2247-2257.
Cai, Z. et al., "Transfected *Drosophila* Cells as a Probe for Defining the Minimal Requirements for Stimulating Unprimed CD8+ T Cells", *Proc. Natl. Acad. Sci. USA*, 1996, 93, 14736-14741.
Corr, M. et al., "T-Cell Receptor-MHC Class I Peptide Interactions: Affinity, Kinetics, and Specificity", *Science*, 1994, 265, 946-949.
DeBruijn, MLH. et al., "Mechanisms of Induction of Primary Virus Specific Cytotoxic T Lymphocyte Responses", *Eur. J. Immunol*, 1992, 22, 3013-3020.
Dillon, Sr. et al., "Vβ5 T Cell Receptors Skew Toward OVA + H-2K b Recognition", *J. Immunol.*, 1994, 152, 1790-1801.
Engelhard VH., "Structure of Peptides Associated with MHC Class I Molecules", *Current Opinion Immunol.*, 1994, 6, 13-23.
Gold, MR. et al., "Biochemistry of B Lymphocyte Activation", *Adv. Immunol.*, 1994, 55, 221-295.
Grupp, SA. et al., "he Phosphatidylinositol Response is an Early Event in the Physiologically relevant Activation of Antigen-Specific B Lymphocytes", *Cell. Immunol.*
Hou, S. et al., "Virus-Specific CD8+ T-Cell memory Determined by Clonal Burst Size", *Nature*, 1994, 369, 652-654.

(Continued)

*Primary Examiner*—Christina Chan
*Assistant Examiner*—F. Pierre VanderVegt
(74) *Attorney, Agent, or Firm*—Woodcock Washburn LLP

(57) ABSTRACT

A new method to capture, purify and expand antigen-specific T lymphocytes has been developed using magnetic beads coated with recombinant MHC class I molecules. This method was optimized using homogenous populations of naive T cells purified from mice transgenic for the 2C T cell receptor (TCR). These T cells were captured on beads coated with MHC class I molecules and the relevant antigenic peptides. MHC and peptide specificity was confirmed by the usage of irrelevant MHC peptide combinations. An enrichment of 800 to 1600 fold was measured, using 2C T cells mixed with irrelevant T cells, starting from a 2C T cell frequency of 1/3000. The same approach was used to purify antigen-specific CD8+ T cells from total CD8+ T cells from naive mice. The recovered cells could be expanded and specifically kill target cells in vitro; they had a significant effect in vivo as well. We expect this procedure to be suitable to purify and expand in vitro tumor- and virus-specific killer T cells for use in cell therapy.

3 Claims, 29 Drawing Sheets

OTHER PUBLICATIONS

Irsch, J. et al., "Switch Recombination in Normal IgA1+B Lymphocytes", *Proc. Natl. Acad. Sci. USA*, 1994, 91, 1323-1327.

Jackson, MR. et al., "Empty and Peptide-Containing Conformers of Class I Major Histocompatibility Complex Molecules Expressed in *Drosophila melanogaster* Cells", *Proc. Natl. Acad. Sci. USA*, 1992, 89, 12117-12121.

Kane, KP. et al., "Class I Alloantigen is Sufficient for Cytolytic T Lymphocytes Binding and Transmembrane Signaling", *Eur. J. Immunol*, 1988, 18, 1925-1929.

Kane, K.P. et al., "Activation of CD-8-Dependent Cytotoxic T Lymphocyte Adhesion and Degranulation by Peptide Class I Antigen Complexes", *J.Immunol.*,1993, 150, 4788-4797.

Kato, K. et al., "Isolation and Characterization of CD34+ Hematopoietic Stem cells from Human Peripheral Blood by High Gradient Magnetic Cell Sorting", *Cytometry*, 1993, 14, 384-392.

Klavinskis, LS. et al., "Efficiency and Effectiveness of Cloned Virus-Specific Cytotoxic T Lymphocytes in Vivo", *J. Immunol*, 1989, 143, 2013-2016.

Kranz, DM. et al., "Attachment of an Anti-receptor Antibody to Non-Target Cells Renders them Susceptible to Lysis by a Clone of Cytotoxic T Lymphocytes", *Proc. Natl. Acad. Sci USA*, 1994, 81, 7922-7926.

Lau, L.L. et al, "Cytotoxic T-Cell Memory Without Antigen", *Nature*, 1994, 369, 648-652.

Luxembourg, A.T. et al., "Modulation of Signaling via the B Cell Antigen Receptor by CD21, the Receptor for C3dg and EBV", *J. Immunol.*, 1994, 153, 4448-4467.

Matsui, K.et al., "Low Affinity Interaction of Peptide-MHC Complexes with T Cell Receptors", *Science*, 1991, 254, 1788-1791.

Mescher, M.F., "Molecular Interactions in the Activation of Effector and Precursor Cytotoxic T Lymphocytes", *Immunol. Rev.*, 1995, 146, 177-210.

Moore, M.D. et al., "Hydrodynamic, Electron Microscopic, and Ligand-Binding Analysis of the Epstein-Barr Virus/C3dg Receptor(CR2)", *J. Biol. Chem.*, 1989, 264, 20576-20582.

Myers, C.D. et al., "Antigen-Induced Changes in Phospholipid Metabolism in Antigen-Binding B Lymphocytes", *J. Immunol.*, 1987, 138, 1705-1711.

Nakanishi, M. et al., "Binding of Cytotoxic T-Lymphocytes to Supported Lipid Monolayers Containing Trypsinizesd H-2K k", *Mol. Immunol.*, 1983, 20, 1227-1231.

Noelle, R.J. et al., "Cognate Interactions between Helper T Cells and B Cells", *Immunol Today*, 1990, 11, 361-368.

Oehen, S. et al., "Antivirally Protective Cytotoxic T Cell Memory to Lymphocytic Choriomeningitis Virus is governed by Persisting Antigen", *J. Exp. Med.*, 1992, 176, 1273-1281.

Radbruch, A. et al., "Detection and Isolation of Rare Cells", *Curr. Opinion Immunol.*, 1995, 7, 270-273.

Ramensee, H.G. et al., "MHC Ligands and Peptide Motifs: First Listing", *Immunogenetics*, 1995, 41, 178-228.

Sawada, K. et al., "Purification of Human Blood Burst-forming Units-Erythroid and Demonstration of the Evolution of Erythropoietin Receptors", *J. Cell. Physiol.*, 1990, 142, 219-230.

Sha, W.C. et al., "Selective Expression of an Antigen Receptor on CD8 Bearing T Lymphocytes in Transgenic Mice", *Nature*, 1988, 335, 271-274.

Snow, E.C. et al., "Activation of Antigen-Enriched B Cells. II. Role of Linked Recognition in B Cell Proliferation to thymus-Dependant Antigens", *J. Immunol.*, 1983, 130, 614-618.

Snow, E.C. et al., "Induction of the c-myc Protooncogene after Antigen Binding to Hapten-Specific B Cells", *J. Exp. Med.*, 1986, 164, 944-949.

Snow, E.C. et al., "Activation of Antigen-Enriched B Cells", *The Journal of Immunolog*, Feb. 1983, 130(2).

Stein, P. et al., "Induction of Antigen-Specific Proliferation in Affinity-Purified Small Lymphocytes: requirement for BSF-1 by Type 2 but not Type 1 thymus-Independent Antigens", *J. Immunol*, 1986, 136, 2080-2089.

Sun, S. et al., "Dual Function of Drosophila Cells as APCs for Naïve CD8+ t Cells: implications for Tumor Immunotherapy", *Immunity*, 1996, 4, 555-564.

Swain, S. et al., "Transforming Growth Factor-$\beta$ and IL-4 cause Helper T-Cell Precursors to Develop Into Distinct effector Helper Cells that Differ in Lymphokine Secretion Pattern and Cell Surface Phenotype", *The Journal of Immunology*, 1991, 147, 2991-3000.

Sykulev, Y. et al., "Kinetics and Affinity of Reactions between Antigen-Specific T Cell Receptor and Peptide-MHC Complexes", 1994, 1, 15-22.

Sykulev, Y. et al., "High Affinity Reactions Between Antigen-Specific T-Cell Receptors and Peptides Associated with Allogeneic and Syngenic Major Histocompatibility Complex Class I Proteins", *Proc. Natl. Acad. Sci. USA*, 1994, 91, 11487-11491.

Tallquist, M.D. et al., "A Single T Cell Receptor Recognizes Structurally Distinct MHC/Peptide Complexes with High Specificity", *J. Exp. Med*, 1996, 184, 1017-1026.

Ukada, K. et al., "Self-MHC-Restricted Peptides Recognized by an Alloreactive T Lymphocyte Clone", *J. Immunol*, 1996, 157, 670-678.

Weber, S. et al., "Specific Low-Affinity Recognition of Major Histocompatibility Complex Plus Peptide by Soluble T-Cell Receptor", *Nature*, 1992, 356, 793-796.

Wilson, H.A. et al., "Crosslinkage of B Lymphocyte Surface Immunoglobulin by Anti-IG or Antigen Induces Prolonged Oscillation of Intracellular Ionized Calcium", 1987, 166, 601-606.

Wunderlich, J. et al., "Induction and Measurement of Cytotoxic T Lymphocyte Activity", *Current Protocols in Immunology*, 1991, 166, 601-606.

Zhang, X. et al., "Control of CD4 Effector Fate: Transforming Growth Factor $\beta$1 and Interleukin 2 Synergize to Prevent Apoptosis and Promote Effector Expansion", *J. Exp. Med*, 1995, 182, 699-709.

Kane, K. et al., "Activation of CD-8 Dependant Cytoloxic T Lymphocyte Adhesion and Degranulation by Peptides Class 1 Antigen Complexes", *Journal of Immunology*, 1993, 150(1), 4700-4797.

Luxembourg, A. et al., "Biomagnetic Isolation of Antigen-Specific Cd8+ T cells Usable In Immunotherapy", *Nature Biotechnology*, 1998, 16(3), 281-285, XP002198433.

Stryhn, A. et al., "Preformed Purified Peptide/Major Histocompatibility Class ! Complexes are Potent Stimulators of Class1-restricted T Cell Hybridomas", *European Journal of Immunology*, Jun. 1994, 24(6), XP008003084.

Nag, B. et al., "Stimulation of T Cells by Antigenic Peptide Complexed with Isolated Chains of Major Histocompatibility Complex Class II Molecules", *Proc. Natl. Acad. Sci. USA*, 1993, 90(4), 1604-1608.

Damle, N.K. et al., "Differential Regulatory Signals Delivered by Antibody Binding to the CD28 (Tp44) Molecule During the Activation of Human T Lymphocytes," *J. Immunology*, 1988, 140(6), 1753-1761.

Boog, Claire J. P. et al., "Specific immune responses restored by alteration in carbohydrate chains of surface molecules on antigen-presenting cells," *Eur. J. Immunol.*, 19, 1989, 537-542.

Marchal, Ingrid et al., "Glycoproteins from Insect Cells: Sialylated or Not?," *Biol. Chem.*, 2001, 382, 151-159.

Tallquist, M. D., et al., "Alloreactive 2C T Cells Recognize a Self Peptide in the Context of the Mutant $K^{bm3}$ Molecule," *J Immunol.*, 1995, 155(5), 2419-2426.

* cited by examiner

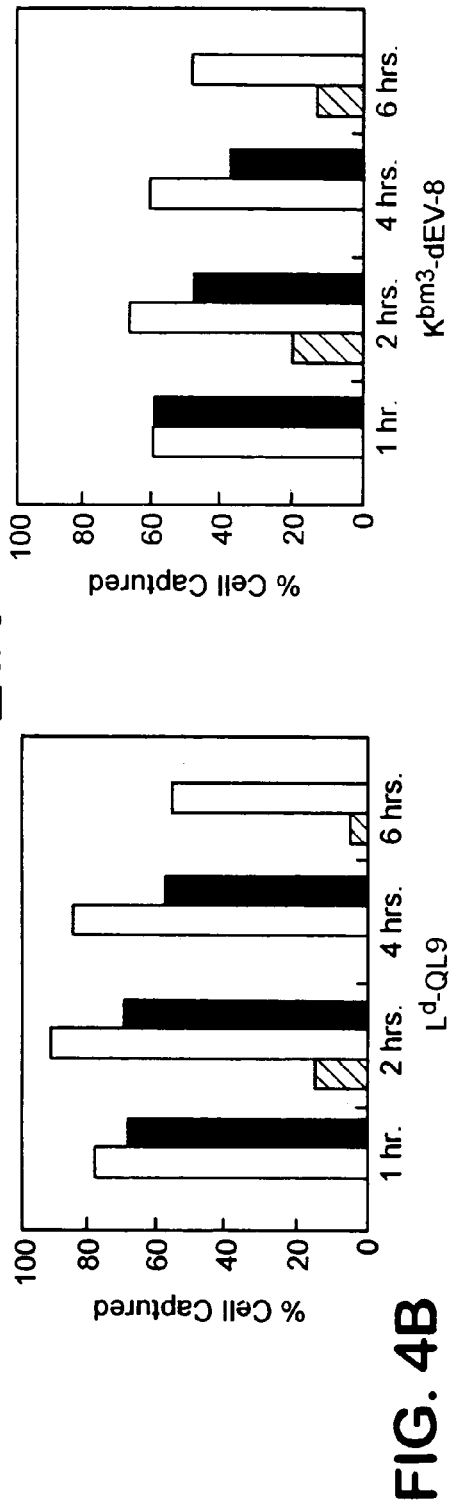
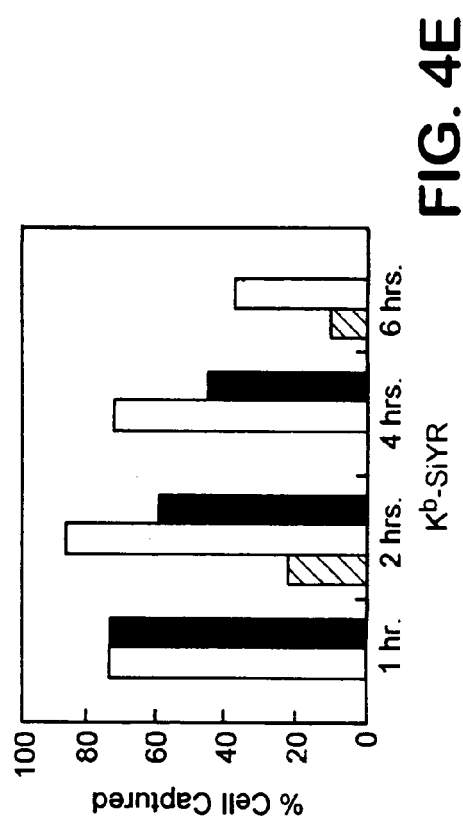
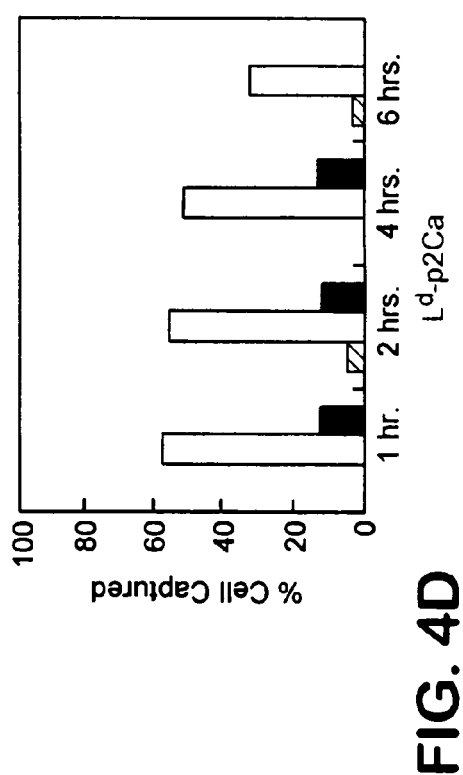
FIG. 4B  FIG. 4C  FIG. 4D  FIG. 4E

PURIFICATION OF ANTIGEN-SPECIFIC T CELLS

CROSS REFERENCE TO RELATED APPLICATIONS

This is a continuation of U.S. application Ser. No. 09/434,965, filed Nov. 5, 1999, now abandoned, which is a divisional of U.S. application Ser. No. 08/909,549, filed Aug. 12, 1997, now abandoned, which claims the benefit of U.S. Provisional Application No. 60/025,588, filed Sep. 6, 1996.

FIELD OF THE INVENTION

This invention is drawn to a method to derive antigen-specific T cell lines from a heterogeneous lymphocyte population, including total T lymphocyte populations of naïve individuals. This method is based on a step of enrichment for antigen-specific lymphocytes by capture of the antigen-specific T lymphocytes on a substrate coated with antigenic peptide-MHC complexes which serve as ligands for specific T-cell antigen receptors, followed by a step of expansion using surfaces coated with antigenic peptide-MHC complexes.

BACKGROUND OF THE INVENTION

Antigen-specific immune responses are mediated by antigen-specific effector B and T lymphocytes. These cells originate from generally low frequency resting precursor cells expressing receptors for various antigens representing the whole repertoire and which, upon encounter with specific antigens and appropriate costimulation, become activated, expand and differentiate into effector cells.

Development of ex vivo immunotherapy for conditions such as cancer or viral infections is limited by the low frequency of antigen-specific precursor lymphocytes. For instance, virus-specific CTL precursor (CTLp) frequencies in the peripheral lymphoid tissues of mice are generally lower than 1/100,000–1/1,000,000 (Lau et al., 1994; Hou et al., 1994). Isolation of antigen-specific lymphocytes by capture on an antigen-coated support has been described for mouse spleen resting B cells specific for TNP (Snow et al, 1983a). The isolation procedure involved a rosetting step on haptenated horse red blood cells and allowed the recovery of hapten-specific B cells with a 40% purity. This technique has been useful to study the requirements for activation (Stein et al, 1986) as well as the initial signaling events following activation (Snow et al, 1986; Myers et al, 1987; Grupp et al, 1987; Noelle and Snow, 1990; Gold and DeFranco, 1994). However, this was a very favorable situation because of the relatively high frequency of B cells specific for TNP (about 1%) (Snow et al,1983a). No study on B cell activation using resting B cells specific for another antigen with low precursor frequency has been reported to date (Radbruch and Recktenwald, 1995).

Low precursor frequency is also a problem with T cells. Additionally, while B cells recognize the antigen directly, T cells recognize a complex structure made of the combination of an antigenic peptide bound to a major histocompatibility complex (MHC) molecule. TCR/MHC-peptide interaction has a low to moderate affinity ($10^{-4}$–$10^{-7}$ M range: Matsui et al, 1991; Weber et al, 1992; Sykulev et al, 1994a; Corr et al, 1994; Sykulev et al, 1994b). Antibodies usually exhibit affinities several orders of magnitude higher and exploit multivalency. New techniques of isolation of rare cell populations are available now. These are based on cell sorting and/or magnetic separation (Bellone et al, 1995; Radbruch and Recktenwald, 1995). Also, recombinant ligands for TCR are now available by combining recombinant empty MHC molecules (Jackson et al, 1992) and MHC-binding antigenic peptides (Engelhard, 1994; Ramensee et al, 1995). These synthetic MHC-peptide complexes can be immobilized on beads to yield multivalent ligands for the TCR. Theoretically, multivalency should help to overcome low affinity. The interaction between TCR and immobilized peptide-MHC complex has been previously shown to lead to the establishment of stable interactions in certain in vitro systems. First, MHC class I antigens immobilized on lipid monolayers (Nakanashi et al, 1983) or on lipid-coated cell-sized beads (Kane et al, 1988) are sufficient to cause binding of cloned allogeneic cytotoxic T cells (CTL). Second, syngeneic cloned CTL bind to MHC-coated beads in a peptide dependent manner (Kane and Mescher, 1993; Mescher, 1995). Third, a cloned syngeneic CTL can form aggregates with RMA-S cells, a cell line which expresses large amounts of empty MHC molecules, in a peptide specific manner (De Bruijn et al, 1992). In two of these reports, TCR-MHC-peptide interactions were not the primary mediator of adhesion. They rather played an initial role in the early events of aggregation, presumably by transducing signals that led to activation of adhesion via accessory molecules.

Here, we describe a method to isolate antigen-specific T cells using empty MHC class I molecules purified from *Drosophila melanogaster* cells (Jackson et al, 1992) immobilized on magnetic beads and loaded with peptide. This artificial substrate for T cells is coated with a high density of identical MHC-peptide complexes. T cell isolation was optimized using populations of naïve T cells purified from mice transgenic for the 2C TCR (Sha et al, 1988). Ligands of various affinities and specificities for the 2C TCR have been identified (Sykulev et al, 1994a, b). 2C T cells could be adsorbed on beads bearing peptide-MHC complexes which had an affinity for the 2C TCR as low as $10^{-4}$ M. Adsorption was MHC restricted and peptide specific since it occurred only with the proper MHC-peptide combinations recognized by the 2C TCR. Additionally, 2C T cells mixed with irrelevant T cells from a naive animal could be recovered using this adsorption procedure. This technique was successfully used to recover antigen-specific T cells from naive animals.

SUMMARY OF THE INVENTION

The present invention provides a method for the isolation and expansion in culture of antigen-specific T lymphocytes from a heterogeneous population of lymphocytes. The present invention also provides a method for preparing a population of antigen-specific T lymphocytes from a patient for treatment of the patient's disease or condition. This invention provides a matrix containing empty Class I peptides which are functional in that the empty Class I peptides can accept and bind a variety of antigens. These matrices can be prepared to contain specific predetermined amounts of one or more antigens. Such matrices are useful for a variety of purposes including, but not limited to, use in the methods of the present invention.

Panel A shows a dose response curve of the mean fluorescence values of beads incubated with increasing amounts of $L^d$, then stained with fluorescein-labeled anti-$L^d$ antibody 30.5.7. Panel B shows green fluorescence (FL1) histograms of unlabeled avidin-coated magnetic beads. Panel C shows green fluorescence (FL1) histograms of avidin-coated magnetic beads after incubation with 3 μg of biotinylated $L^d/10^6$ beads; staining was performed using fluorescein-labeled anti-$L^d$ antibody 30.5.7. Panel D shows green fluorescence (FL1) histograms of avidin-coated magnetic beads after incubation with 3 μg of non-biotinylated $L^d/10^6$ beads; staining was performed using fluorescein-labeled anti-$L^d$ antibody 30.5.7.

FIG. 2 Panels A, B, C, D, E and F: Assessment of $L^d$-coated bead-2C T cell complex formation in the presence of antigenic peptides using green (FL1) versus red (FL2) fluorescence dot plots. Cells were stained in green with fluorescein; beads were stained in red with phycoerythrin. Magnetic beads are autofluorescent; compensation was set so that phycoerythin stained beads displayed the same green fluorescence intensity as unstained beads. Panel A shows beads alone. Panel B shows 2C T cells alone. Panel C shows $L^d$-coated beads and 2C T cells incubated in the presence of QL9. Panel D shows $L^d$-coated beads and 2C T cells incubated in the presence of p2Ca. Panel E shows $L^d$-coated beads and 2C T cells incubated in the presence of SL9. Panel F shows $L^d$-coated beads and 2C T cells incubated in the presence of LCMV peptide.

FIG. 3 Panels A, B, C, D, E, F, G and H: Assessment of MHC-coated bead-2C T cell complex formation in the presence of antigenic peptides using side scatter (SSC) versus forward scatter (FSC) dot plots. Panel A: shows boundaries of the regions containing the cells, the beads, and the cell-beads complexes. Panel B shows beads alone. Panel C shows 2C T cells alone. Panel D shows $L^d$-coated beads and 2C T cells incubated in the presence of QL9. Panel E shows $L^d$-coated beads and 2C T cells incubated in the presence of p2Ca. F: $L^d$-coated beads and 2C T cells incubated in the presence of LCMV peptide. Panel G shows $K^{bm3}$-coated beads and 2C T cells incubated in the presence of dEV-8. Panel H shows $K^{bm3}$-coated beads and 2C T cells incubated in the presence of E1.

Figure 4A:
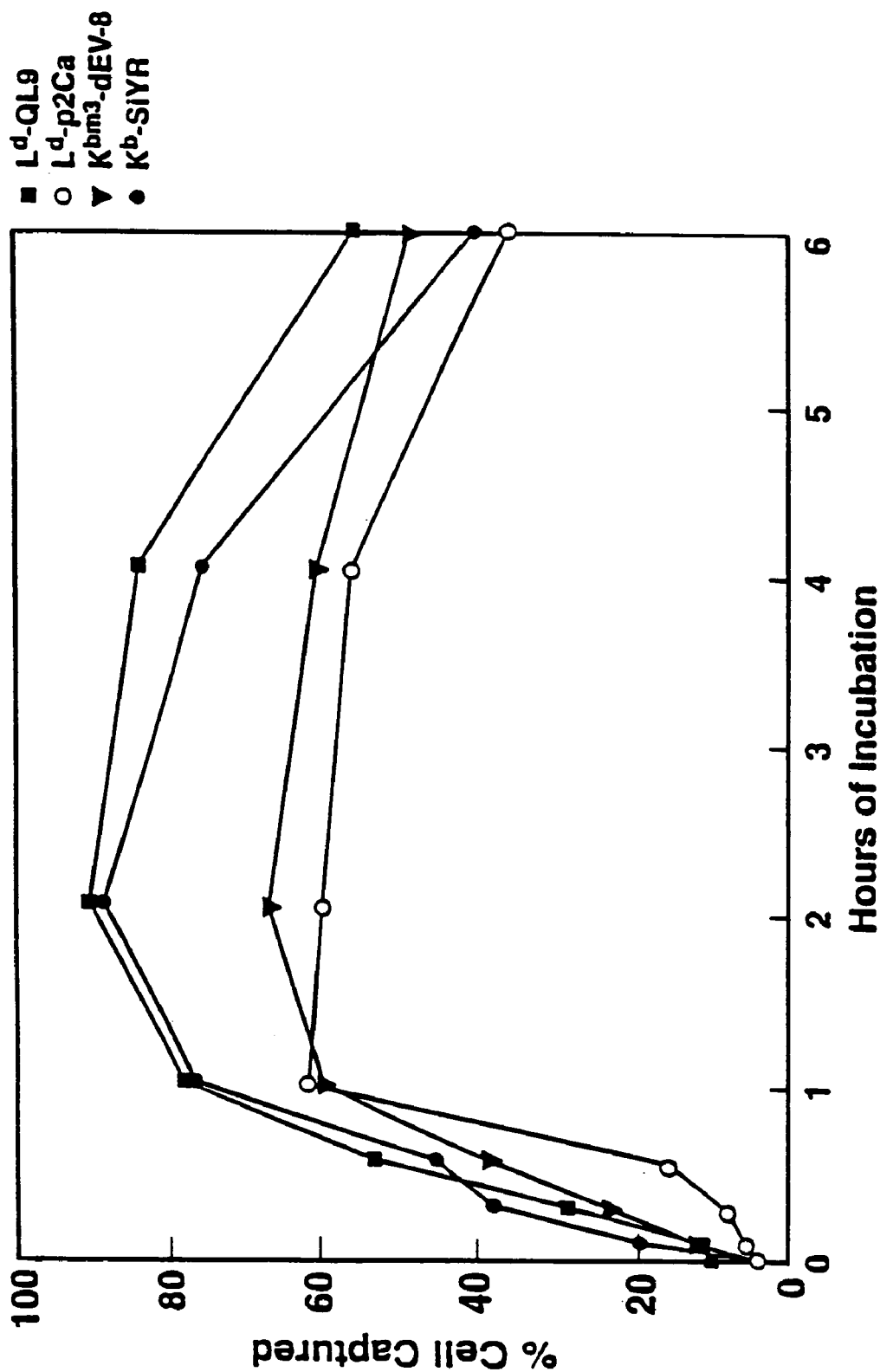
Figure 4F:
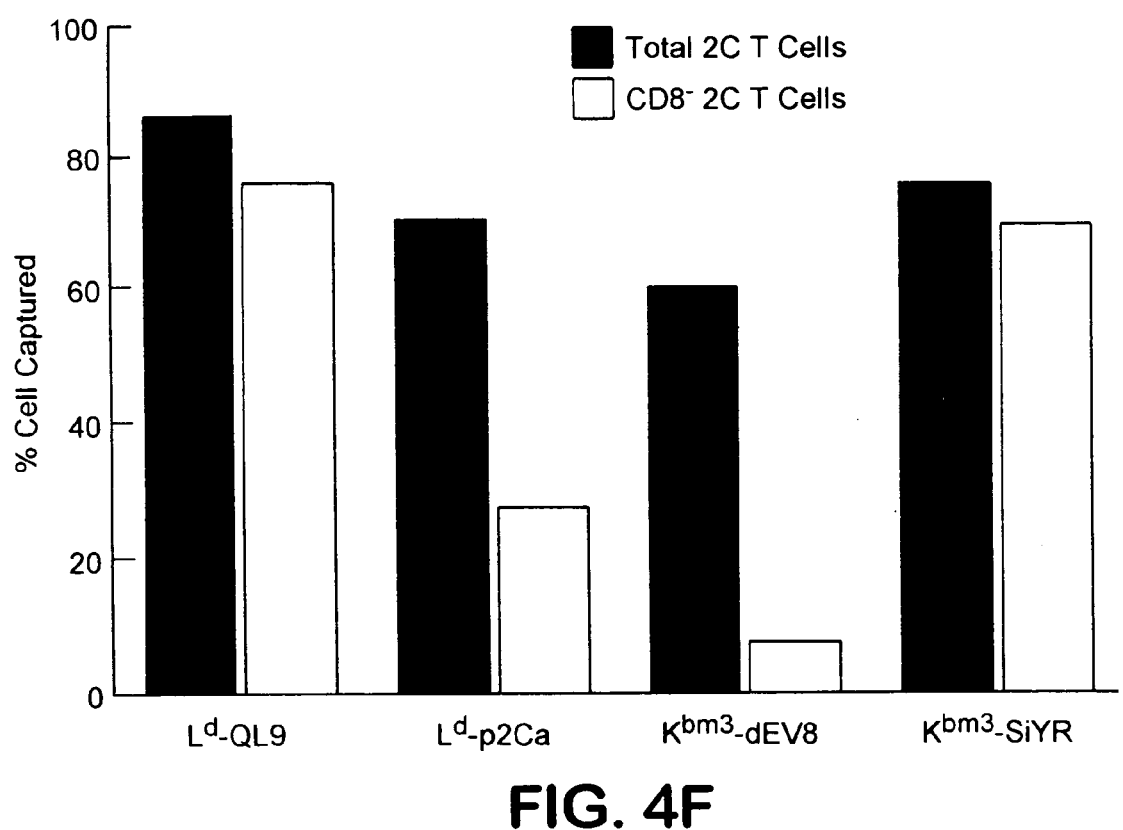
Figure 5A:
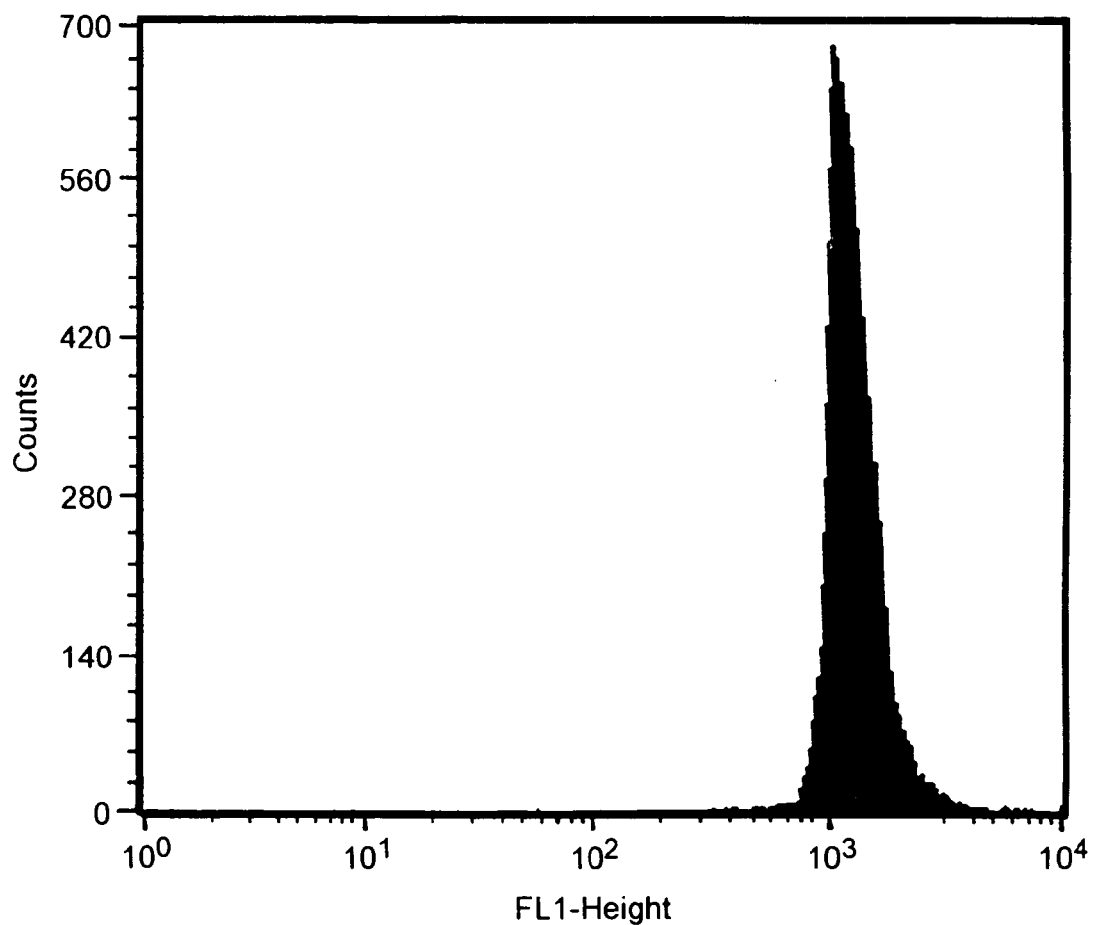
Figure 5B:
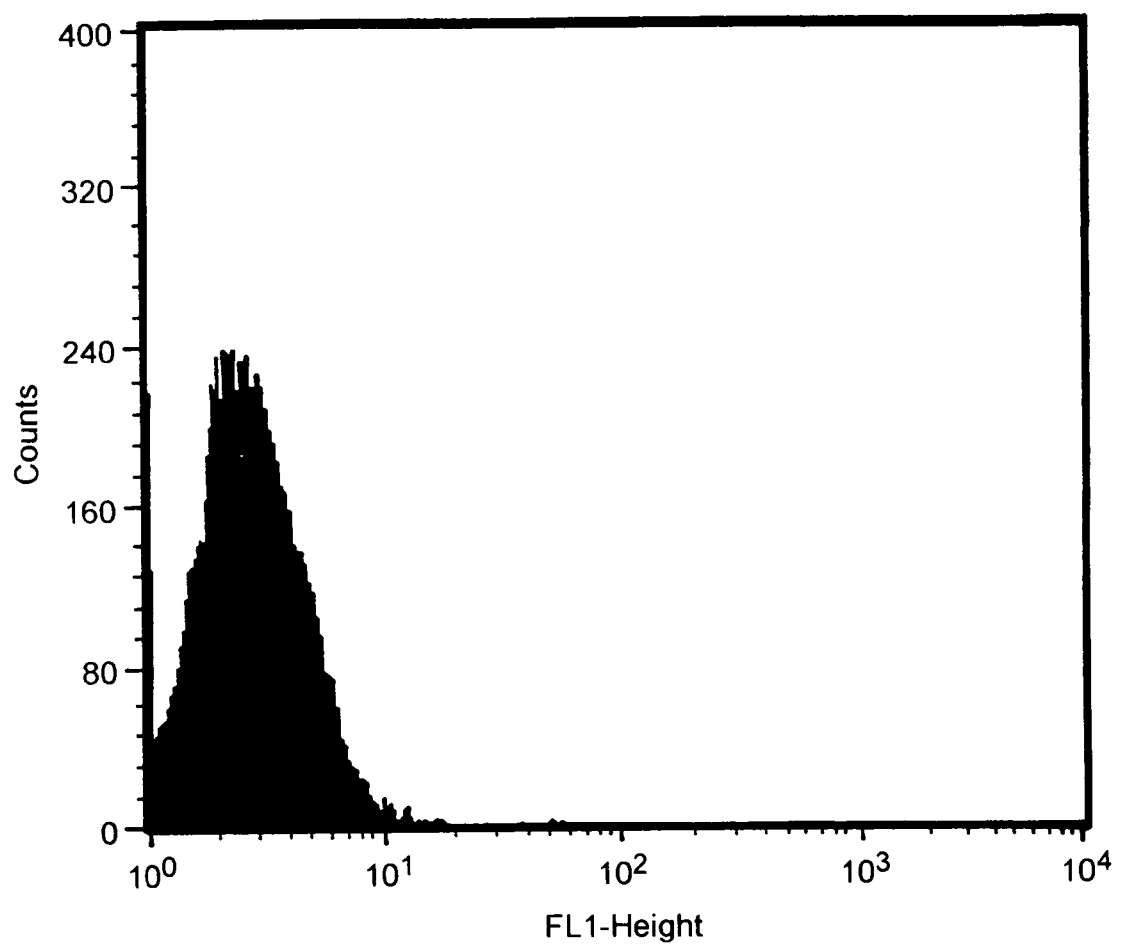
Figure 5C:
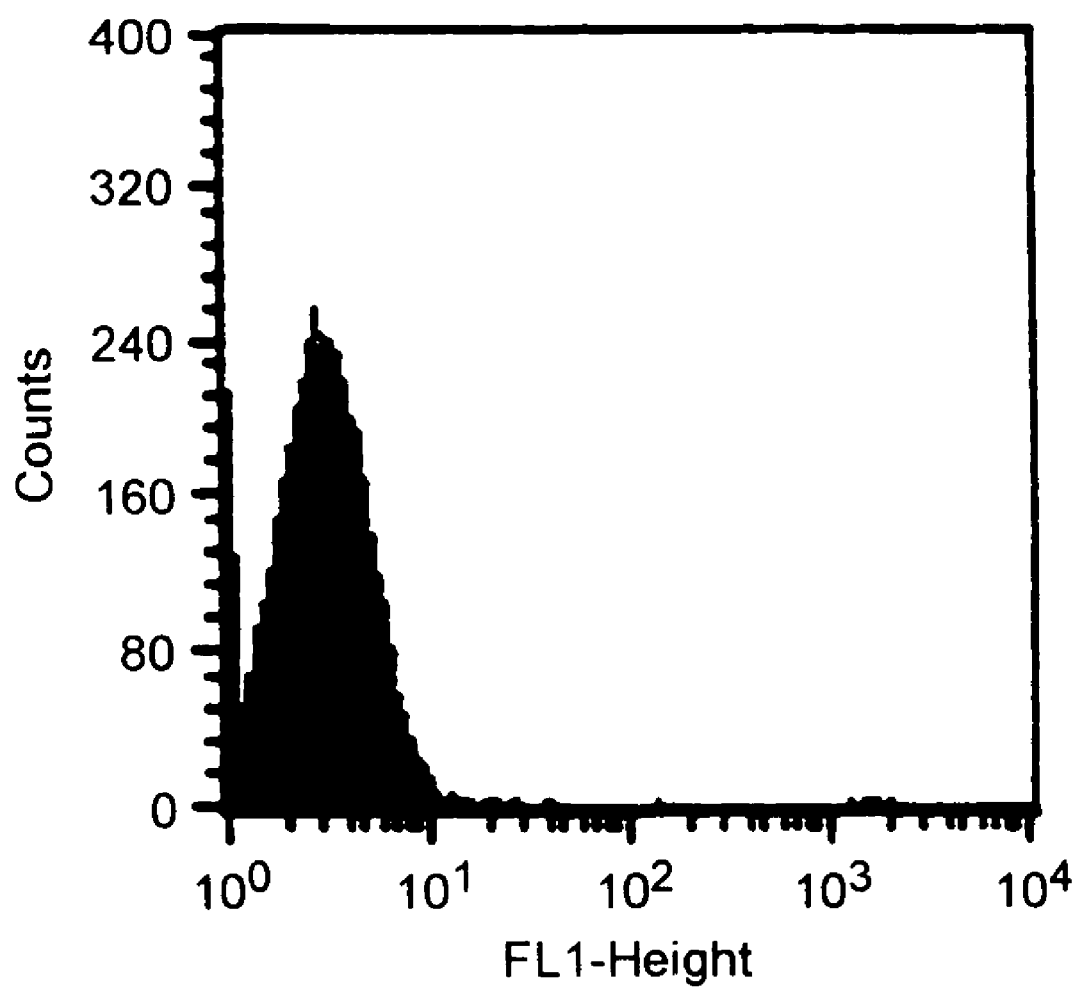
Figure 5D:
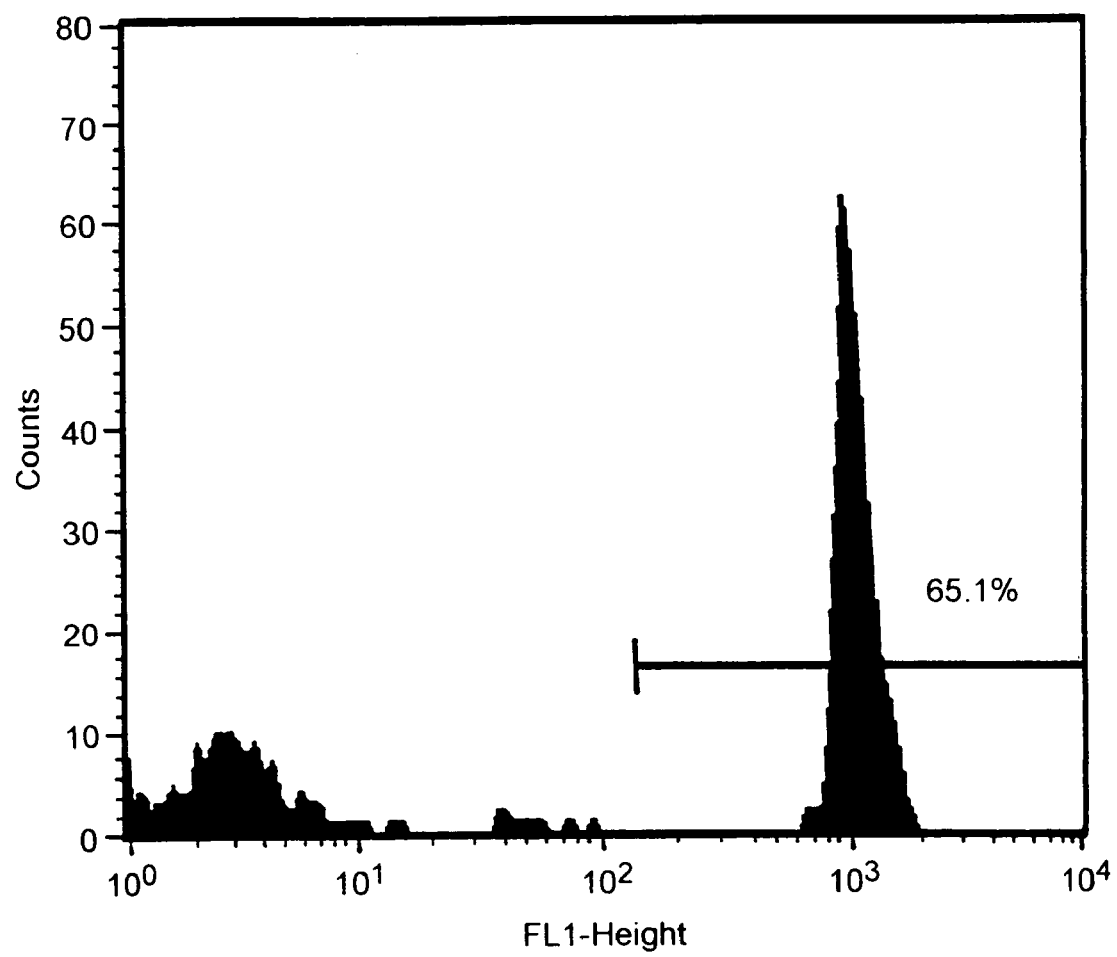
Figure 5E:
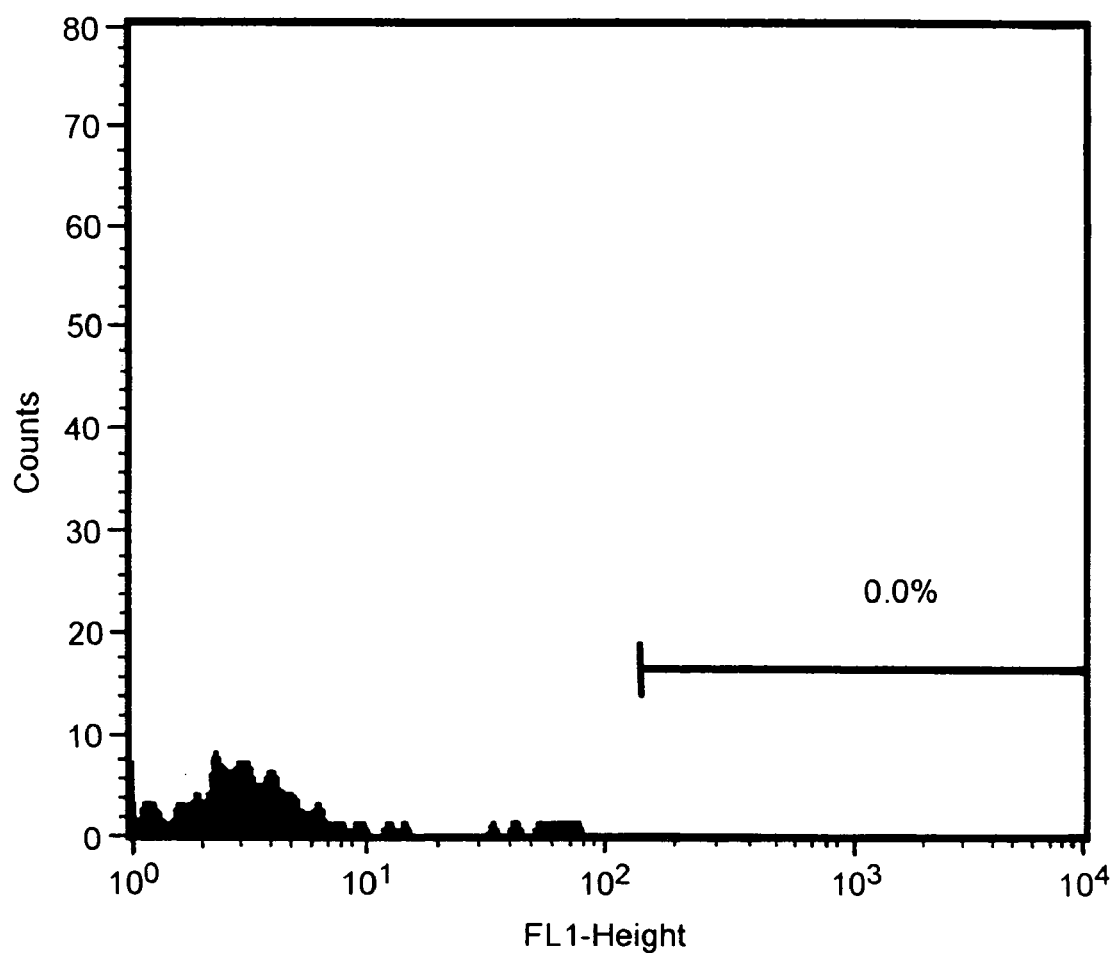

FIG. 4 Panels A, B and C: effect of various parameters on 2C T cell adsorption onto MHC-coated magnetic beads. Panel A shows time dependence: purified 2C T cells were mixed with MHC-coated beads and peptide, and incubated at room temperature for various amounts of time; cell attachment was then quantified by flow cytofluorometry. Panel B shows temperature dependence: purified 2C T cells were mixed with MHC-coated beads and peptide, and incubated at various temperatures and for various amounts of time; cell attachment was then quantified by flow cytofluorometry. Panel C shows CD8 dependence: purified 2C T cells or purified CD8⁻ 2C T cells were mixed with MHC-coated beads and peptide, and incubated at room temperature for 3 hours; cell attachment was then quantified by flow cytofluorometry.

FIG. 5 Panels A, B, C, D and E: enrichment in 2C T cells using capture on $K^{bm3}$-coated magnetic beads, starting with a mixture of 2C T cells and CD8⁺ T cells at a ratio of 1:3000. Panel A shows green fluorescence (FL1) histogram of fluorescein-labeled purified 2C T cells. Panel B shows green fluorescence (FL1) histogram of purified CD8⁺ T cells from C57BL/6 mouse. Panel C shows green fluorescence (FL1) histogram of purified fluorescein-labeled 2C T cells mixed with CD8⁺ T cells from C57BL/6 mouse at a ratio of 1:3000. Panel D shows green fluorescence (FL1) histogram of cells eluted after incubation with $K^{bm3}$-coated magnetic beads in the presence of dEV-8. Panel E shows green fluorescence (FL1) histogram of cells eluted after incubation with $K^{bm3}$-coated magnetic beads in the presence of E1.

FIG. 6: in vitro functional activity of CTL derived from naïve C57BL/6 mouse using adsorption on $K^b$-OVA-8 or $K^b$-VSV-8-coated magnetic beads. Cultured T cells were tested for cytotoxicity by chromium release assay as indicated in Example 4. EL4 cells were used as targets. Peptides were used at a final concentration of 1 μM.

FIG. 7: in vitro functional activity of CTL derived from naïve BALB/c mouse using adsorption on $L^d$-LCMV-coated magnetic beads. Cultured T cells were tested in vitro for cytotoxicity by chromium release assay as indicated in Example 4. $L^d$-expressing RMA-S (panel A), BALB/c CL-7 (panel B), MC57 (panel C) or YAC-1 (panel D) were used as targets. Peptides were used at a final concentration of 1 μM.

Figures 8A, 8B:
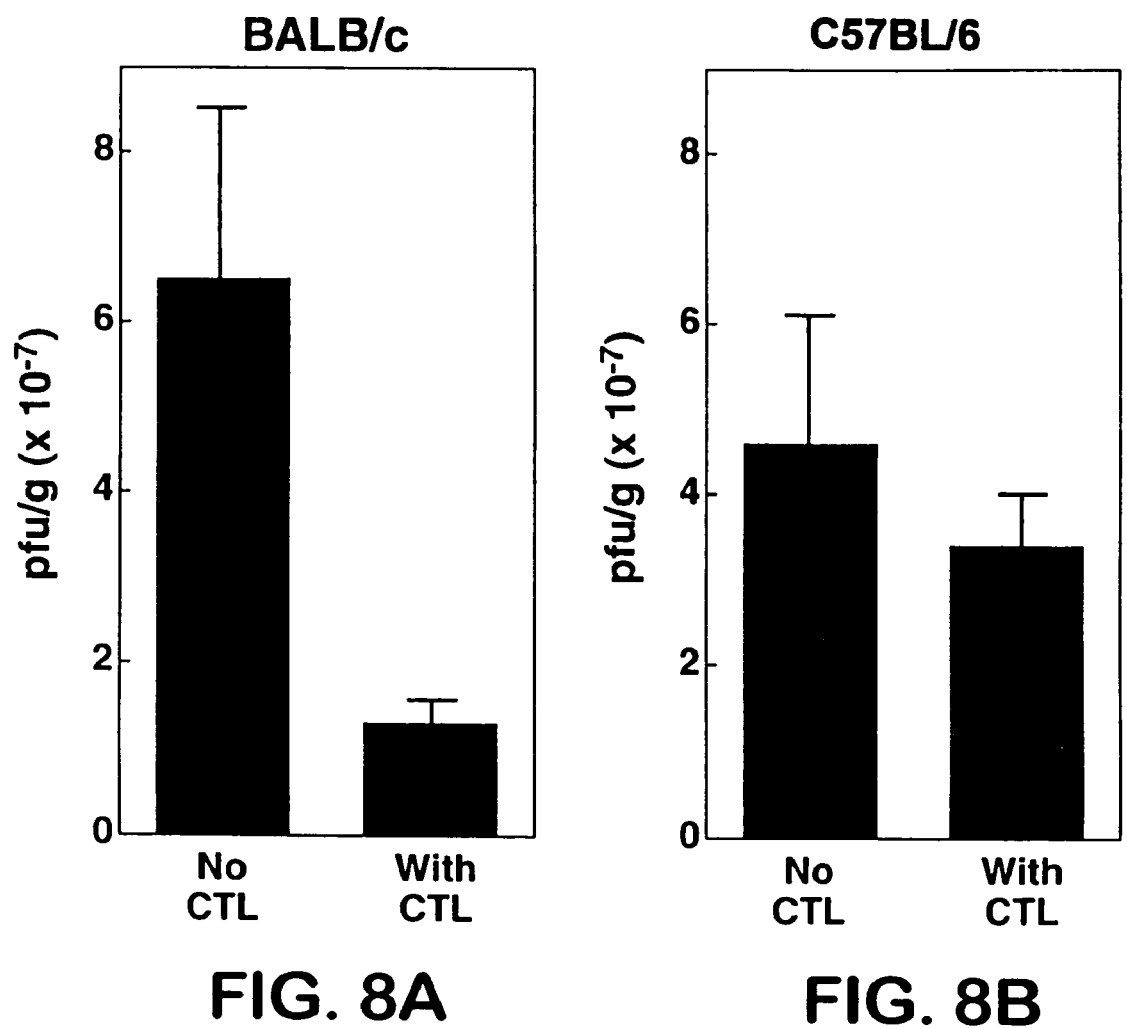

FIG. 8: in vivo functional activity of CTL derived from naïve BALB/c mouse using adsorption on $L^d$-LCMV-coated magnetic beads. In vivo activity in mice acutely infected with LCMV was assayed as indicated in Example 4. LCMV-infected BALB/c mice were injected with $10^7$ CTL anti-LCMV NP 118–126 at day 1, while 4 BALB/c mice received only PBS. As a control we used LCMV-C57BL/6 mice injected with either $10^7$ CTL anti-LCMV NP 118–126 or PBS.

DETAILED DESCRIPTION OF THE INVENTION

The present invention provides a new method to derive in vitro antigen-specific T cell lines from mixed cell populations, including total T cells from naïve individuals. Deriving T cell lines in vitro from naïve T cell populations poses several types of problems: first, the precursor frequencies are typically very low, often lower than $10^{-5}$; second, naïve T cells have special requirements for activation, needing generally stronger stimuli than previously activated T cells.

The method of the present invention comprises two steps: one step of isolation to enrich the cell preparation in antigen-specific T cells, and one step of in vitro expansion to derive antigen-specific cell lines from the enriched cell preparation. It is readily apparent to those skilled in the art that these steps may be repeated, as desired. The step of isolation of antigen-specific T cells utilizes MHC-coated substrates, which upon incubation with antigenic peptide and T cells, enabled isolation of T cells specific for the antigenic peptide-MHC complex. It will be readily apparent to those skilled in the art that a wide variety of MHC molecules are suitable for use in the method of the present invention, including, but not limited to, classical and non-classical MHC proteins from any mammalian or avian species, with human HLA proteins and murine H-2 proteins being preferred. It will also be readily apparent to those skilled in the art that MHC molecules from a variety of sources are suitable for use in the present invention, including, but not limited to, MHC derived from naturally occurring sources and from recombinant sources such as MHC proteins expressed in bacteria, insect cells or mammalian cells, with insect cells being preferred. In addition, it will be readily apparent to those skilled in the art that a wide variety of MHC coated substrates are suitable for use in the present invention, including, but not limited to, columns (acrylamide, agarose, . . . ), glass beads, latex beads, membranes (nitrocellulose, nylon, . . . ), plastic (e. g., polystyrene) surfaces such as microtitration plates, high molecular weigh polysaccharides such as dextrans, red blood cells, and magnetic beads, with magnetic beads being preferred. Finally, it will be readily apparent to those skilled in the art that a wide variety of procedures could be used to attach MHC molecules on substrates for use in the method of the present invention, including, but not limited to, passive adsorption, use of cross-linkers, biotinylation of MHC molecules for adsorption on avidin-coated substrate, introduction of a recognition site by genetic engineering of MHC molecules or use of natural recognition site for adsorption on antibody-coated substrate, with avidin-biotin and antibody recognition being preferred.

To establish the procedure, combination of several resources was utilized: first, we used empty recombinant MHC molecules produced in Drosophila melanogaster cells (Jackson et al, 1992), which allowed the use of MHC protein homogeneously loaded with the same peptide; second, naive T cells purified from lymph nodes of mice transgenic for the 2C TCR (Sha et al, 1988) were used, these cells homogeneously express the same TCR at the same level. This allowed analysis at a single cell level. Also several different peptide-MHC complexes whose affinities for the 2C TCR have been recently determined (Sykulev et al, 1994a, b) were used. This made it possible to investigate the procedure using complexes with various affinities. The MHC class I molecules that were used included $L^d$, $K^b$ and $K^{bm3}$. Since the 2C cytotoxic T cell clone was derived from BALB.B (H-$2^b$) mice (Sha et al, 1988), $L^d$ and $K^{bm3}$ are allogeneic restriction elements for the 2C TCR while $K^b$ is syngeneic. Immobilized biotinylated $L^d$, $K^b$ and $K^{bm3}$ on avidin-coated magnetic beads were used. 2C T cells were absorbed on such beads in the presence of several antigenic peptides. Adsorption was observed in the presence of peptide-MHC complexes with an affinity for the 2C TCR in a $10^{-4}$–$10^{-7}$ M range, using $L^d$, $K^{bm3}$ or $K^b$ as restriction element. Finally adsorption was specific, since control peptides did not cause interaction between MHC-coated beads and 2C T cells.

The characteristics of adsorption of T cells onto MHC-coated beads were further studied: adsorption was time dependent, reaching a plateau between 1 and 4 hours when performed at room temperature. Adsorption started to decrease beyond that time, which might reflect the initiation of a de-adhesion process. Adsorption was also temperature dependent: it was slightly lower at 37° C. than at room temperature for 3 of the peptide-MHC complexes examined, and was even dramatically lower than at room temperature for another one. This is due to the decrease in stability of MHC molecules at higher temperature. Adsorption at 4° C. was much lower than at room temperature which was likely a consequence of the changes in cell membrane fluidity at low temperature which reduces molecular associations. Additionally, some signaling events, which occur only at higher temperature, might contribute to adsorption, as noted in a previous report about the role of CD8 in adhesion induced by TCR-antigen interaction (Kane and Mescher, 1993). Interestingly, CD8 dependence of cell-bead complex formation varied according to the antigen used. Among the peptides tested, the most CD8-dependent were p2Ca and dEV-8, which had been isolated as naturally occurring at the surface of antigen presenting cells; QL9 and SIYR, which have not been found on cell surface, were CD8 independent. In any case, CD8 dependence of T cell capture on MHC-coated beads was not completely correlated with TCR-ligand affinity. Finally, capture was not completely correlated with TCR-ligand affinity, since we consistently observed capture with $K^{bm3}$-dEV-8 ($1.8\times10^4$ $M^{-1}$), $K^b$-SIYR ($3.1\times10^4$ $M^{-1}$) or $K^{bm3}$-SIYR ($3.4\times10^4$ $M^{-1}$), but not with $L^d$-p2Ca-A3 ($2\times10^4$ $M^{-1}$) or $K^b$-dEV-8 ($1.2\times10^4$ $M^{-1}$). Capture was observed or not with $L^d$-SL9 ($1.4\times10^4$ $M^{-1}$), according to $L^d$ batches. This is consistent with the prediction that knowing the affinity of a single TCR for a given peptide-MHC complex is probably not enough to make predictions about interactions at the whole cell level (Agrawal and Linderman, 1996). It is anticipated that MHC-coated beads will be useful as probes to study the rules of antigen recognition by T cells.

To investigate the suitability of this technique to recover a low frequency population of antigen-specific CTL precursors, it was attempted to recover 2C T cells mixed with irrelevant T cells from a naive animal. It was shown that the procedure of the present invention allowed the purification of antigen-specific T cells about 800 to 1600 fold in one step of purification, starting from a 2C T cell frequency as low as 0.03%. Cell recovery was about 50% when using peptide-MHC complexes of low affinity for the 2C TCR such as $K^{bm3}$-dEV-8 and $K^b$-SIYR, and reached 90–100% with the high affinity $L^d$-QL9 complex. Final 2C T cell purity was 47.6±2.1% when using $K^b$, the syngeneic restriction element for the 2C TCR, and 24.8±6.9% when using $L^d$, an allogeneic restriction element. This suggests that this difference could be accounted for by anti-$L^d$ allogeneic T cells captured using $L^d$-coated beads. This would mean that some of the non-2C cells eluted from the beads had been captured specifically. Taken together, these results showed that this method was suitable to purify low frequency T cell precursors from a naive animal, including cells whose TCR would have a low affinity for an MHC-peptide complex.

It was also shown that the isolation procedure of the present invention, when used in combination with a new in vitro T cell expansion step, was usable to enrich in CTL precursors from naive mice. The cell expansion step was based on the culture of isolated cells in tissue culture plates coated with MHC-peptide complexes and anti-CD28 antibody. It will be readily apparent to those skilled in the art that other costimulatory molecules are suitable for use in the method of the present invention, including, but not limited to, anti-CD28 antibody, other ligands of CD28 such as B7-1 and B7-2, or ligands or antibodies to other T cell costimulatory molecules such as integrins and other cell adhesion molecules, or cytokines such as interleukin-2 or interleukin-4, or any combination thereof. It is noteworthy that other classical expansion protocols, including stimulation with concanavalin A or with anti-TCR antibody, would not allow antigen-specific CTL to be derived from naïve lymphocyte populations. This is likely because the cells are not 100% pure after isolation and thus need some specific stimulation to be recovered. Additionally, a high density of homogeneous ligands is necessary to activate unprimed T cells, which is provided by the method of the present invention, as well as by using MHC-expressing insect cells as antigen-presenting cells (Cai et al., 1996), but not by using classical antigen presenting cells which present a heterogeneous population of antigens on their surface. Additionally, this totally synthetic expansion system of the present invention does not require use of exogenous antigen-presenting cells, which eliminates potential complications such as contamination and cross-priming. Interestingly, it was not necessary to detach the cells from the MHC-coated magnetic beads used for isolation prior to expansion, which reduces the time of manipulation. However, the antigen-specific T lymphocytes may be eluted or removed from the substrate for culturing or for other purposes, if desired. The T lymphocytes may be eluted using a variety of techniques known to those skilled in the art, such as prolonged incubation and/or addition of an anti-MHC antibody. Using this method, LCM virus-specific CTL could be derived from uninfected BALB/c mice using $L^d$-coated magnetic beads and LCMV-nucleoprotein peptide. Enrichment certainly had occurred since at least one cell in the $10^4$ cells recovered was antigen-specific, as compared to a precursor frequency of less than $10^{-5}$ in a naive animal (Oehen et al 1992, Lau et al, 1994). Additionally, unseparated total $CD8^+$ T cells from the same animal cultured in the same conditions did not yield specific CTL activity. Finally, specific CTL activity was measured after only one restimulation, which strongly indicates a high frequency of specific precursor T cells following the enrichment procedure. We also used the enrichment procedure of the present invention to recover OVA-8 specific CTL as well as VSV-8 specific CTL from C57BL/6 mice. Enrichment was specific since no VSV-8-specific CTL could be grown from cells captured using $K^b$-OVA-8-coated beads, and no OVA-8-specific CTL could be grown from cells captured using $K^b$-VSV-8-coated beads. The CTL precursor frequency of OVA-8 specific CTL in the enriched population after capture on $K^b$-OVA-8-coated beads was approximately 1/3500. Enrichment thus certainly had occurred since the precursor frequency for CTL anti-OVA-8 in naive C57BL/6 mice is 1/30,000 (Dillon et al., 1994). However, enrichment appeared to be lower than expected from the experiments using 2C T cells (Table II). This is not surprising because measurements with 2C T cells reflect directly the capability of the enrichment step, whereas, in experiments starting from total $CD8^+$ T cells, enrichment was likely underestimated: some $CD8^+$ cells might have been captured and expanded without displaying a cytotoxic activity, or might have been captured but would not grow in culture, or might have a too weak interaction with MHC-coated beads to be "capturable". It is unlikely that capture makes T cells unresponsive because 2C T cells can be expanded into CTL after capture.

Magnetic separation has proven to be the method of choice to purify rare cell populations. These include human peripheral blood hemopoietic progenitor cells (purification from 0.18% to 54.4%, 300 fold enrichment, >39% recovery) (Kato and Radbruch, 1993), human peripheral blood burst-forming units-erythroid (purification from 0.04% to 56.6%, 1400 fold enrichment, 13% recovery) (Sawada et al, 1990), and peripheral blood $IgA_1$-expressing B lymphocytes (purification from 0.1–1.5% to up to 80%, up to 80% recovery) (Irsch et al, 1994). The method of the present invention for antigen-specific T cell enrichment is substantially better than these methods, as judged by the enrichment and recovery numbers. This is especially significant since the purification methods mentioned above used antibodies as ligands for the specific cells; antibodies have affinities for antigens that are much higher than those of MHC-peptide complexes for TCR. The method of the present invention is also useful for cell purification via other low affinity ligands to cell surface molecules, low affinity ligands meaning molecules that have an affinity too low to remain stably bound to cell surface when used in soluble form. In contrast, high affinity ligands, such as antibodies, remain stably bound on cell surface when used in soluble form.

Interestingly, although fluorescent labeling of antigen-specific T cells is possible (Altman et al., 1996), cell sorting by flow cytometry could not be a substitute for magnetic separation because T cell precursors are usually too rare to be detectable in flow cytometry, and the speed of analysis and sorting remains a limiting factor. In contrast, magnetic separation can be used to separate rare antigen-specific T cell populations, as well as to sort large numbers of cells quickly. These features make magnetic isolation an attractive procedure to derive antigen-specific T cells for clinical use.

In conclusion, this is the first report of a method of purification of antigen-specific T cells that is applicable to naïve individuals. We showed that it could be applied to several different MHC molecules and a variety of peptides. The method of the present invention is usable in a variety of situations, including, but not limited to, the use to derive virus- or tumor-specific cytotoxic T cell lines from human peripheral blood. The cells derived using the method of the present invention are themselves useful for a variety of purposes including, but not limited to, expansion in culture and reinfusion into a patient, diagnostic analysis, and other therapeutic applications.

The following Examples are provided for the purpose of illustrating the present invention without, however, limiting the scope of the present invention to the following examples.

EXAMPLE 1

Attachment of Biotinylated MHC Class I Molecules on Avidin-coated Magnetic Beads Soluble MHC class I molecules $L^d$, $K^b$ and $K^{bm3}$ were expressed in *Drosophila melanogaster* cells (Jackson et al, 1992) and purified as previously described (Sykulev et al, 1994a). Biotinylation was performed using biotin-BMCC (Pierce, Rockford, Ill.) according to the manufacturer instructions.

Dynabeads M500 (Dynal, Lake Success, N.Y.) were coated with neutravidin (Pierce, Rockford, Ill.), and subsequently incubated with biotinylated MHC class I molecules diluted in PBS containing 3% FCS for 2 hours at 4° C. under mild agitation. Beads were then washed 3 times in DMEM containing 10% FCS and incubated for 1 hour with 20 μM peptide. Beads were then used immediately for cell adsorption.

Figure 1A:
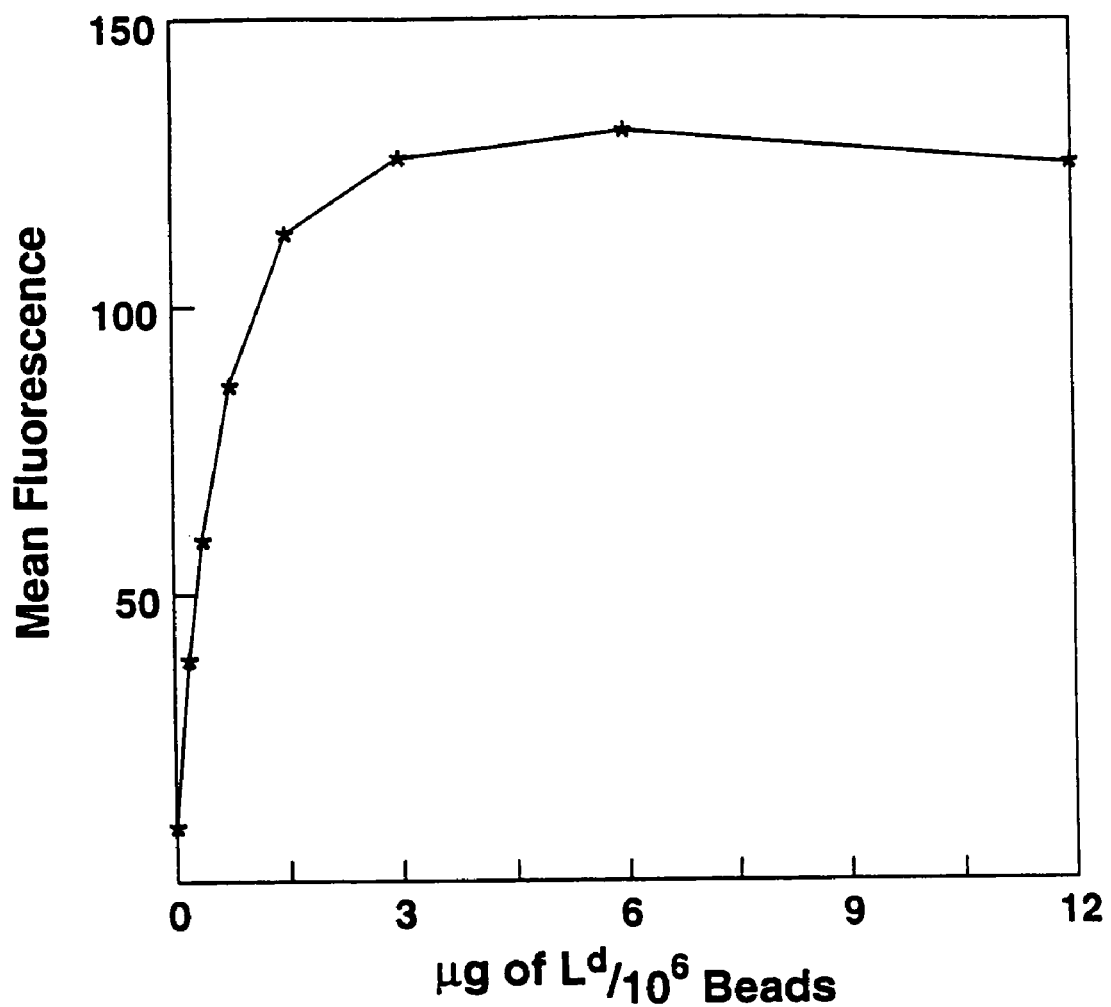
FIG. 1 Panels A, B, C and D: Analysis of binding of biotinylated $L^d$ to avidin-coated magnetic beads using flow cytofluorometry.

Biotinylated $L^d$ was used as a test model to study attachment of biotinylated MHC class I to avidin-coated magnetic beads. Various amounts of this molecule were incubated with beads. Beads were then stained using fluorescein-labeled conformation sensitive anti-$L^d$ monoclonal antibody 30.5.7. Attachment of $L^d$ was assessed by flow cytofluorometry analysis. The mean fluorescence value increased linearly with the amount of $L^d$ between 0 and 1.5 μg of $L^d/10^6$ beads, and reached a plateau at 3 μg of $L^d/10^6$ beads as shown in FIG. 1A. The amount of $L^d$ required to reach saturation was the same with several batches of beads and of biotinylated $L^d$.

Figure 1B:
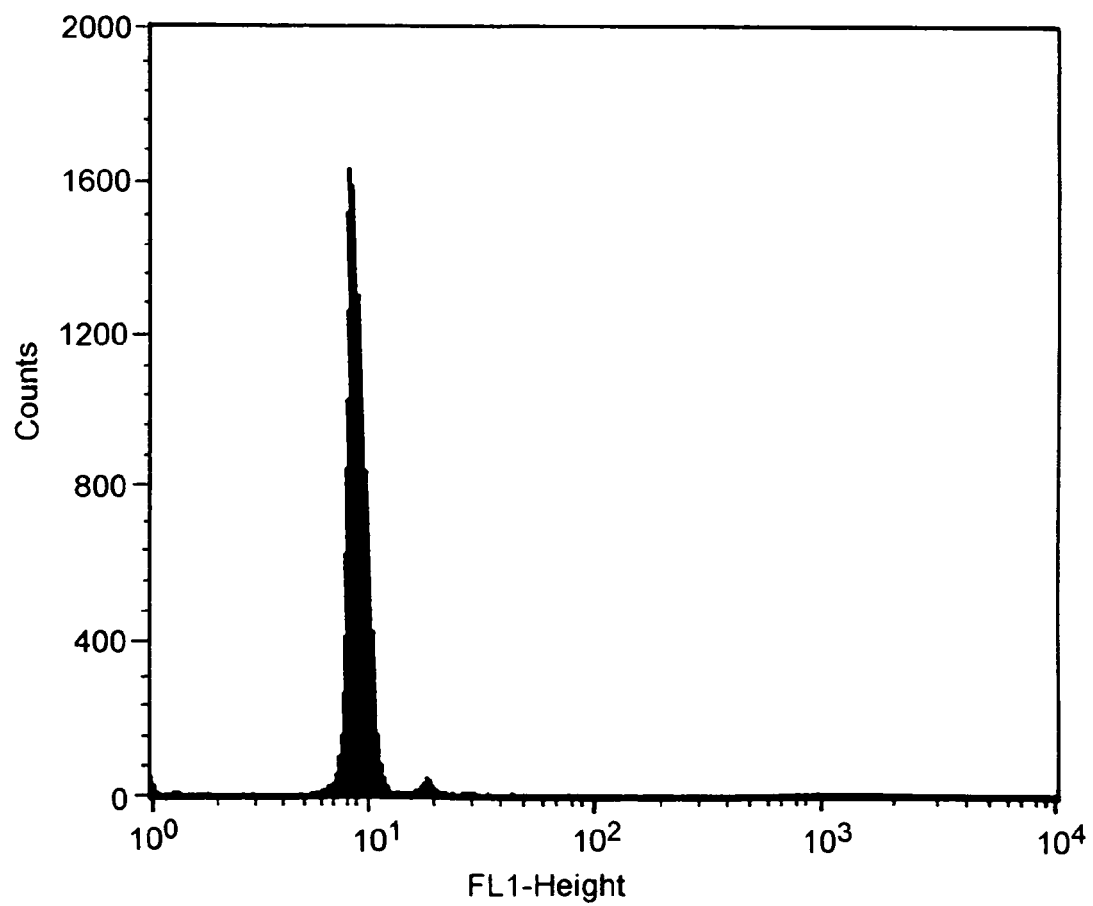
Figure 1C:
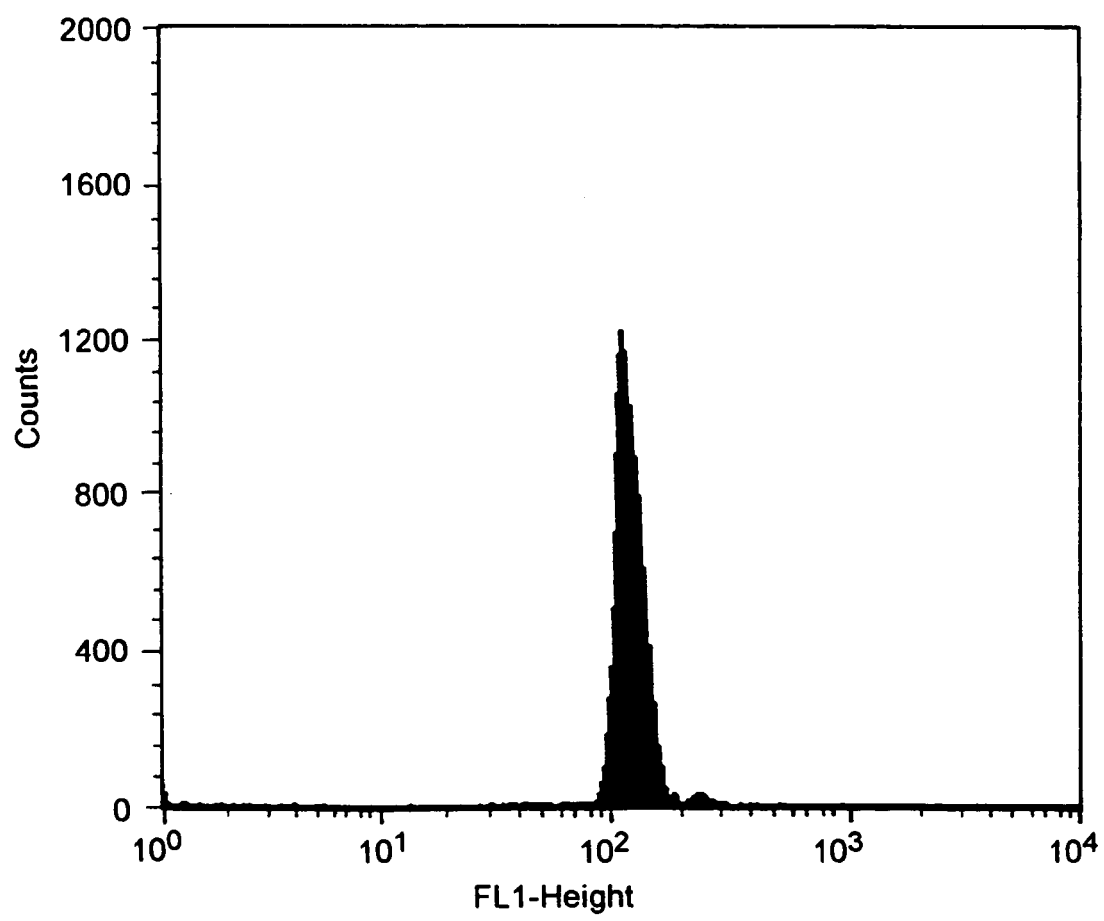
Figure 1D:
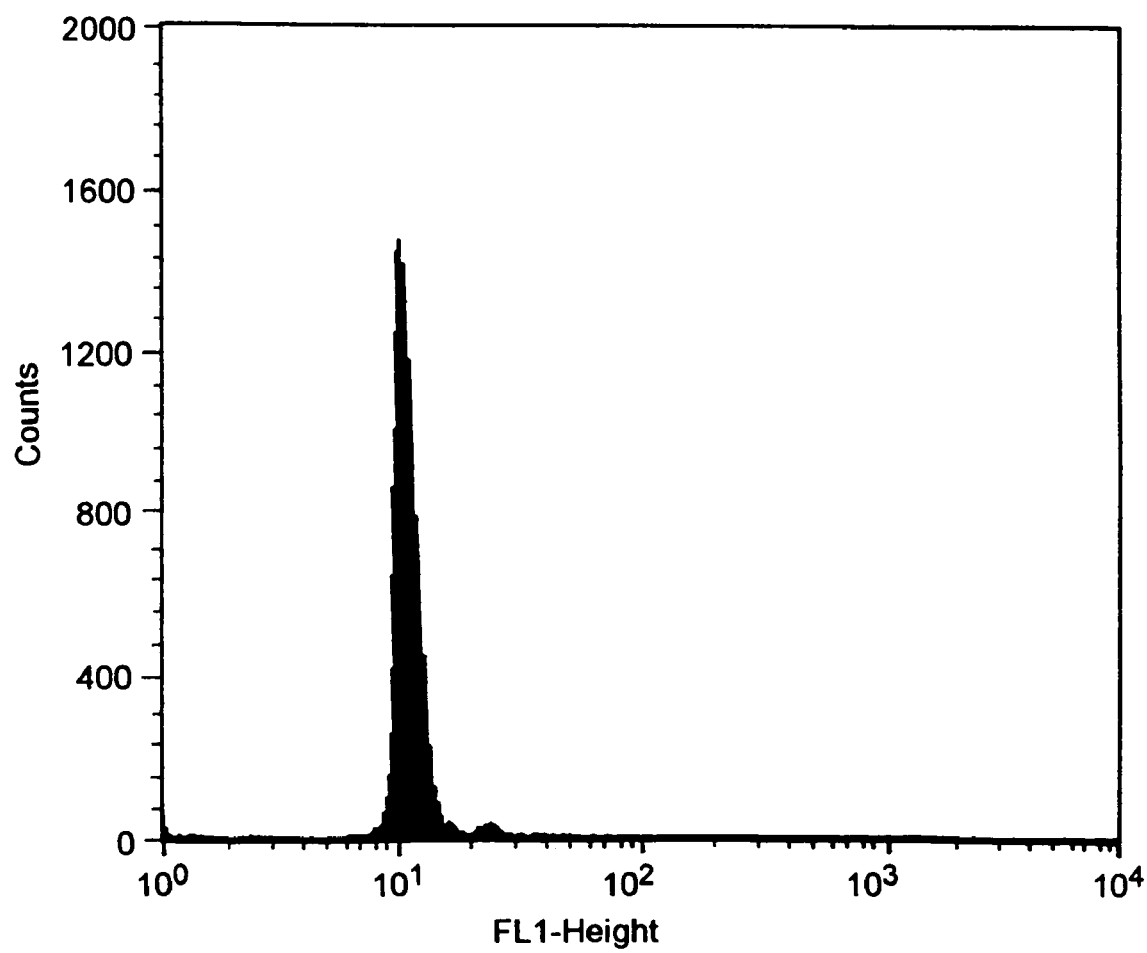

To quantitate the number of MHC molecules immobilized per bead, we measured the concentrations of MHC class I molecules in solution before and after binding by using a solid phase immunoassay as follows: MHC class I molecules $L^d$ was adsorbed on 6.8 μm polystyrene latex sulfate beads (Interfacial Dynamics Corporation, Portland, Oreg.) that had been coated with 28-14-8S anti-$L^d$ (ATCC, Rockville, Md.); beads were then stained using fluorescein-labeled 30-5-7 anti-$L^d$; mean fluorescence values (MFV) were measured by flow cytofluorometry. A standard curve was established with known concentrations of $L^d$ and MFV was plotted versus concentrations. The amount of immobilized $L^d$ in saturating conditions was found to be $1.23 \pm 0.10 \times 10^6$ molecules per bead. Fluorescence histograms show fluorescence of unstained beads (FIG. 1B) and of beads adsorbed with saturating amounts of $L^d$ (FIG. 1C). Attachment occurred via avidin-biotin interaction since non-biotinylated molecules did not bind to beads (FIG. 1D). $K^b$ and $K^{bm3}$-coated beads were prepared and tested using the same technique. Saturation was achieved using the same range of concentrations as for $L^d$.

EXAMPLE 2

Capture of Antigen-specific T cells onto MHC Class 1-coated Magnetic Beads in the Presence of Antigenic Peptides Mice and cell lines. BALB/c ($H-2^d$) and C57BL/6 ($H-2^b$) mice were from Harlan Sprague Dawley (San Diego, Calif.). 2C transgenic mice (Sha et al, 1988) were bred in R. W. Johnson P.R.I. vivarium. All mice were kept under specific pathogen free conditions. $L^d$-expressing RMA.S cells (Cai and Spent, 1996), and EL4 cells ($H-2^b$, obtained from ATCC, Rockville, Md.) were used as target cells in CTL assays. The anti-clonotypic 1B2 hybridoma was previously described (Kranz et al., 1994).

Purification of CD8$^+$ T Cells from Normal Mice

Purification was performed at 4° C. under sterile conditions. Mouse inguinal, axillary, cervical, iliac and mesenteric lymph nodes were dissected and separated into single cell suspension. Avidin-coated magnetic beads (Dynal, Lake Success, N.Y.) were coated with biotinylated goat anti-mouse Ig (Southern Biotechnology, Birmingham, Ala.), and then incubated with the cell suspension to adsorb Ig-expressing cells. Non-adsorbed cells were then incubated with 2 µg/ml H129.19 (anti-CD4, Gibco BRL, Gaithersburg, Md.), 1 µg/ml AF6-120.1 (anti-I-$A^b$, Pharmingen, San Diego, Calif.), 1 µg/ml KH74 (anti-I-$A^b$, Pharmingen, San Diego, Calif.) and 1 µg/ml 34-5-3 (anti-I-$A^{d,b}$, Pharmingen, San Diego, Calif.) for mice with an $H-2^b$ background; or with 2 µg/ml H129.19 and 1 µg/ml 34-5-3 for mice with an $H-2^d$ background. Cells were then washed 3 times and cells expressing CD4 or MHC-class II were eliminated by adsorption on sheep anti-rat Ig-coated magnetic beads (Dynal, Lake Success, N.Y.). Purity reached 90 to 94% of CD8$^+$ cells as judged by antibody staining and flow cytofluorometry.

Purification of 2C T Cells from 2C Transgenic Mice

2C T cells were purified from mouse lymph nodes according to the procedure described above. Purified cells were 97–98% reactive with the anti-clonotypic antibody 1B2. Additionally, CD8$^-$ (CD4$^-$) cells could also be prepared by removing the CD8$^+$ cells with the anti-CD8a antibody 53-6.7 (Gibco-BRL, Gaithersburg, Md.) and magnetic beads coated with sheep-anti-rat Ig.

Peptides

The $L^d$- and $K^b$-binding peptides used in these studies were synthesized on Applied Biosystem 430A and 431A instruments by standard solid phase peptide synthesis method (tBoc chemistry). The peptide sequences were as follows:

| | | |
|---|---|---|
| QL9: | QLSPFPFDL | [SEQ. ID. NO.: 1] |
| p2Ca: | LSPFPFDL | [SEQ. ID. NO.: 2] |
| SL9: | SPFPFDLLL | [SEQ. ID. NO.: 3] |
| p2Ca-A3: | LSAFPFDL | [SEQ. ID. NO.: 4] |
| dEV-8: | EQYKFYSV | [SEQ. ID. NO.: 5] |
| SIYR: | SIYRYYGL | [SEQ. ID. NO.: 6] |
| LCMV: | RPQASGVYM | [SEQ. ID. NO.: 7] |
| MCMV: | YPHFMPTNL | [SEQ. ID. NO.: 8] |
| OVA-8: | SIINFEKL | [SEQ. ID. NO.: 9] |
| VSV-8: | RGYVYQGL | [SEQ. ID. NO.: 10] |
| E1: | EIINFEKL | [SEQ. ID. NO.: 11] |

2C T Cell Adsorption on MHC-coated Magnetic Beads

To test the capacity of MHC class I-coated beads to capture antigen-specific T cells, we used magnetic beads coated with $L^d$, $K^{bm3}$ or $K^b$, and T cells purified from 2C TCR transgenic mice. The 2C TCR has been extensively characterized and several antigenic peptides, recognized with various affinities in association with $L^d$ (Table I), have been reported (Sykulev et al, 1994 a, b). Moreover, $K^{bm3}$ and $K^b$ have recently been shown to serve as restriction elements for the 2C TCR in association with the peptides dEV-8 and SIYR (Tallquist and Pease, 1995; Ukada et al, 1996; Tallquist et al., 1996). It has been recently determined that the affinities of $K^{mb3}$-dEV-8 and $K^b$-SIYR complexes for the 2C TCR were $1.8 \times 10^4$ M$^{-1}$ and $3.1 \times 10^4$ M$^{-1}$ respectively. Unless stated otherwise, beads were coated with saturating amounts of biotinylated $L^d$, $K^{bm3}$ or $K^b$ molecules.

Cells were suspended with beads to reach a final concentration of $10^7$ beads/ml. Cell concentrations were $10^6$/ml in FIGS. 2, 3 and 4, and $10^7$/ml in FIGS. 5, 6 and 7. Peptides were added at a concentration of 20 µM. Adsorption was performed under mild agitation for the time durations and under the temperatures indicated in the text. Cells adsorbed to beads were then counted under the microscope. In cases where a definite rosette (3 beads or more per cell) was not observed, attachment was tested by gently tapping the coverslip. Upon incubation at room temperature in the presence of the high affinity peptide QL9, intermediate affinity peptide p2Ca and low affinity peptide SL9, the majority of 2C T cells attached to $L^d$-coated beads, as judged by microscopic examination after 4 hours of incubation (Table I). Similar results (60–80% of cells captured) were obtained in 5 independent experiments. Cell attachment was specific since it did not occur in the presence of non-2C reactive $L^d$-LCMV and $L^d$-MCMV complexes.

Figure 2A:
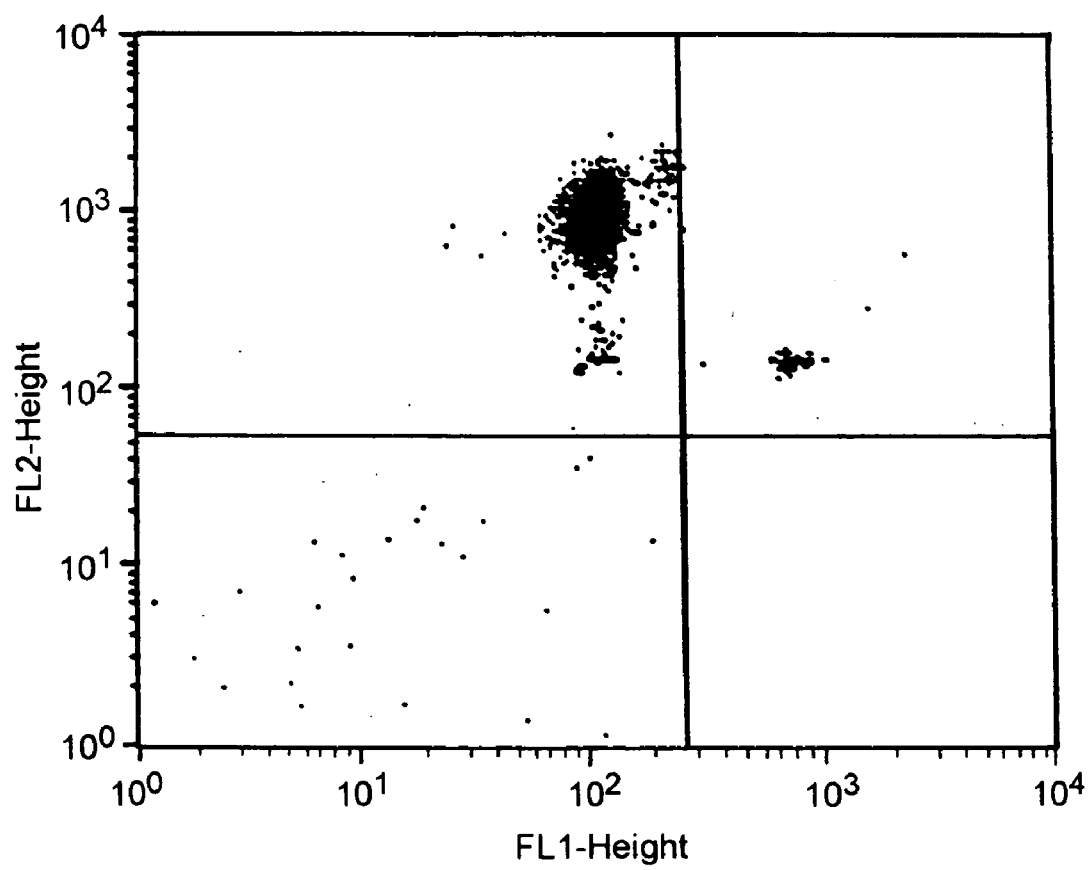
Figure 2B:
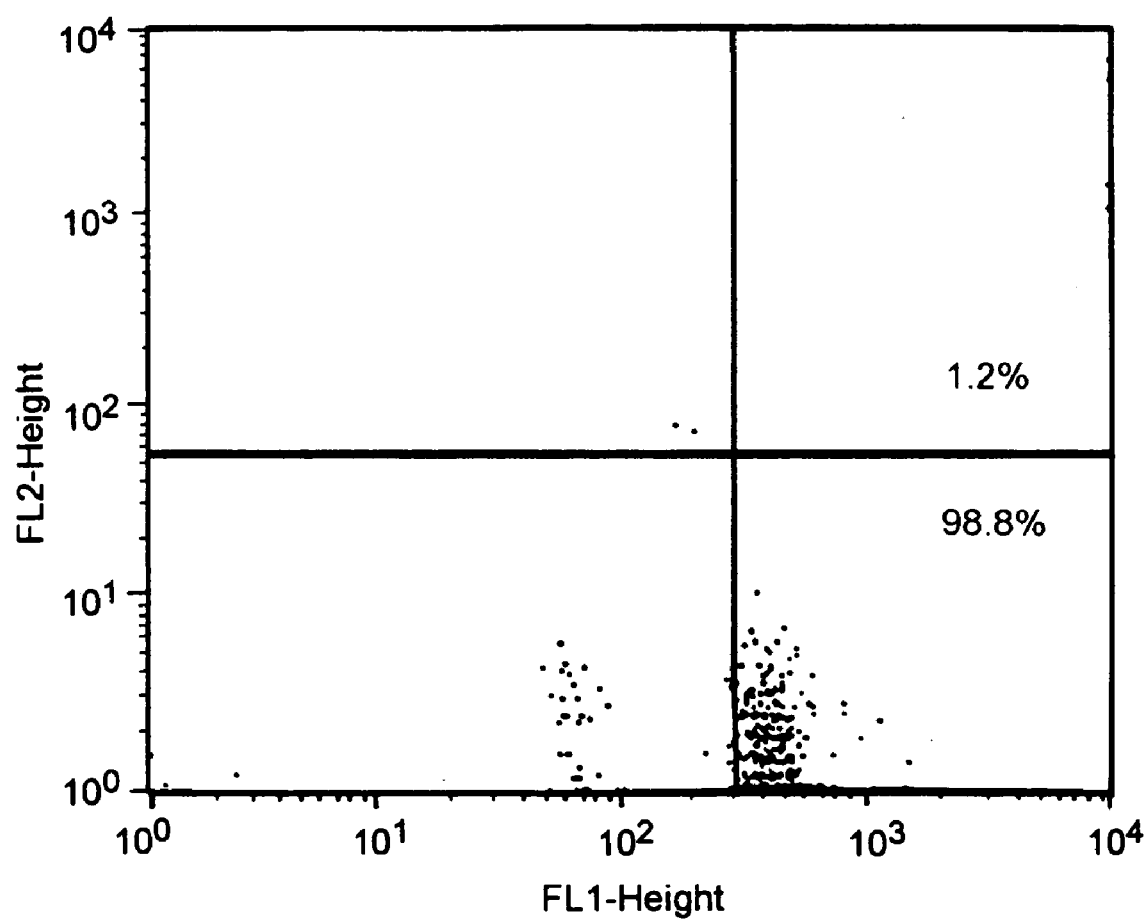
Figure 2C:
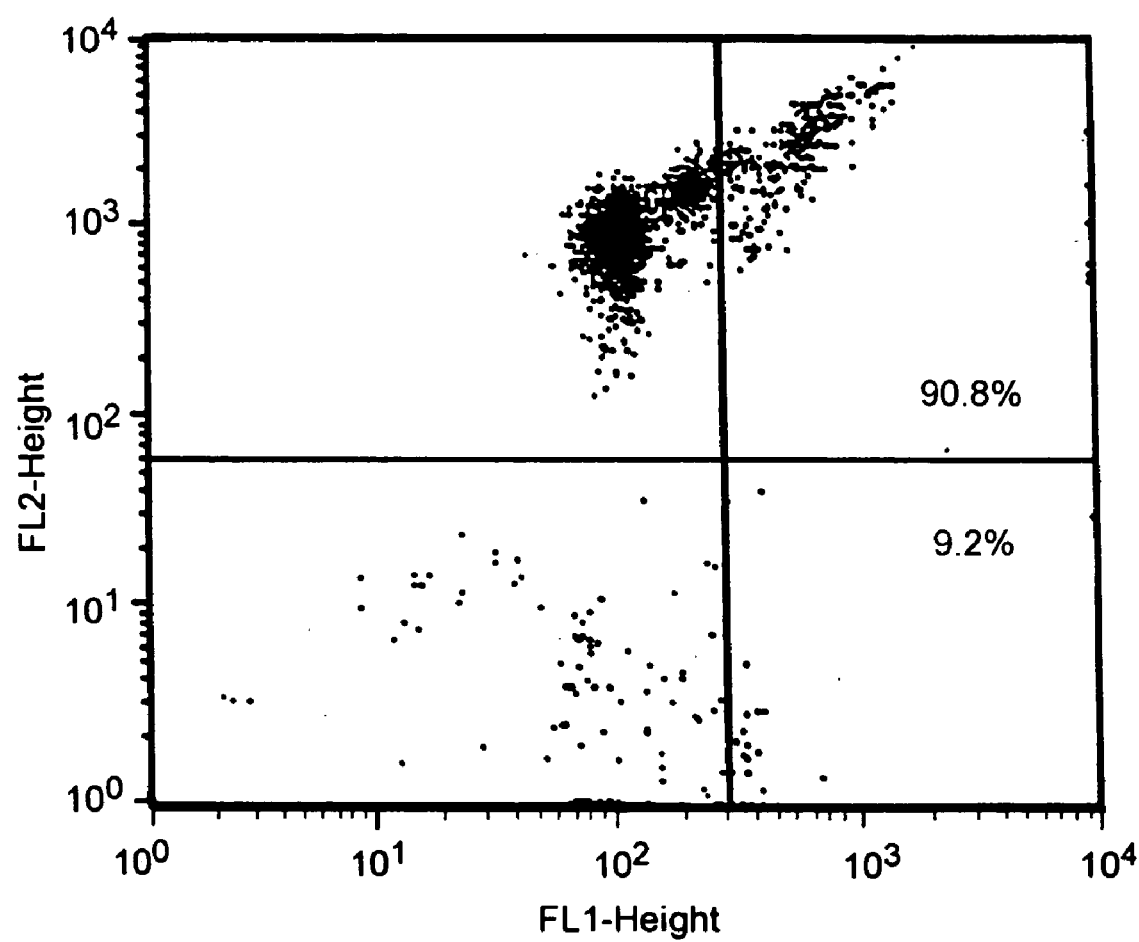
Figure 2D:
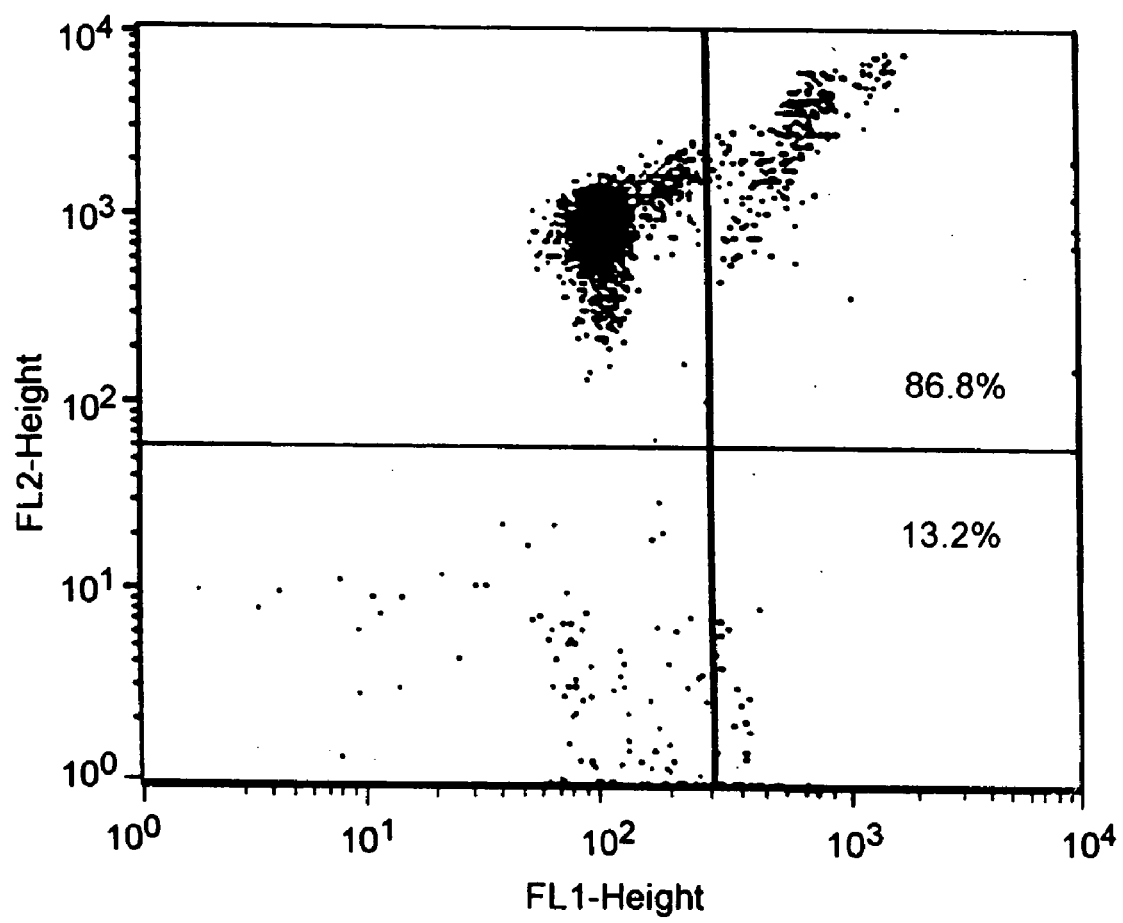
Figure 2E:
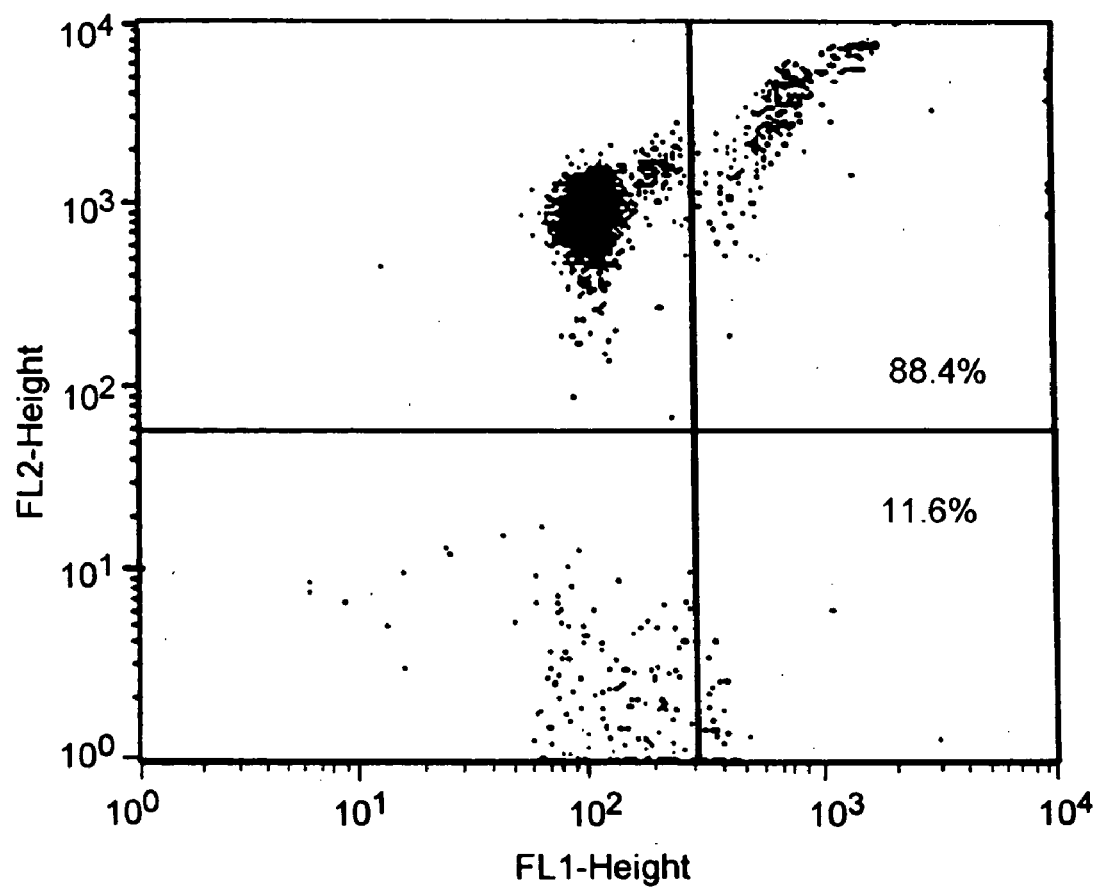
Figure 2F:
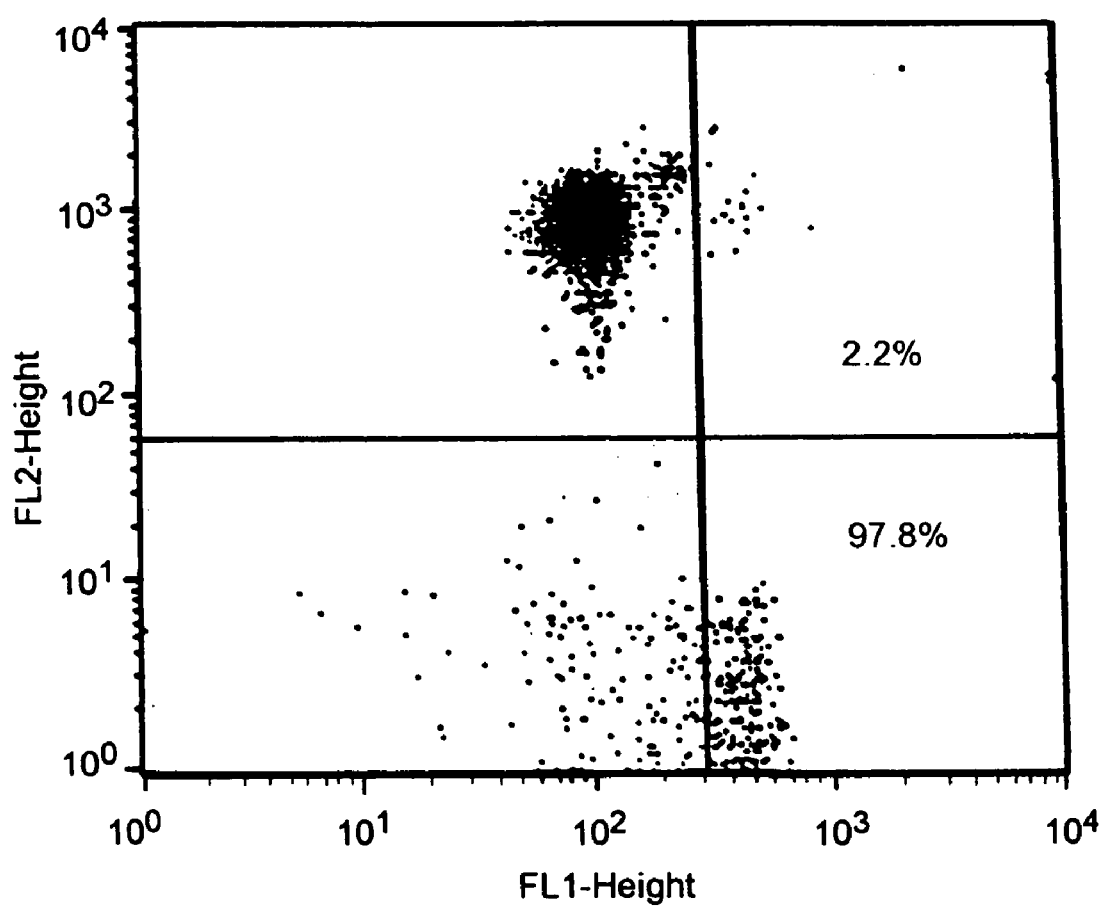
Figure 3A:
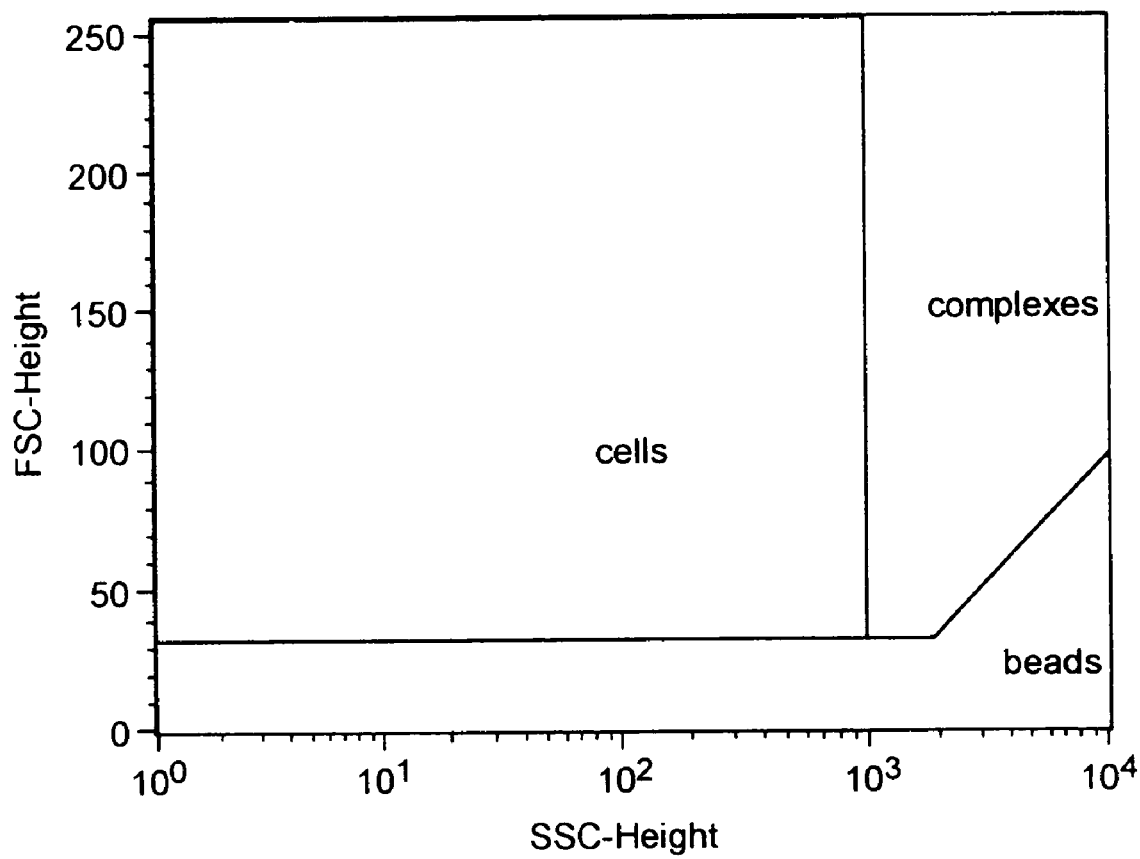
Figure 3B:
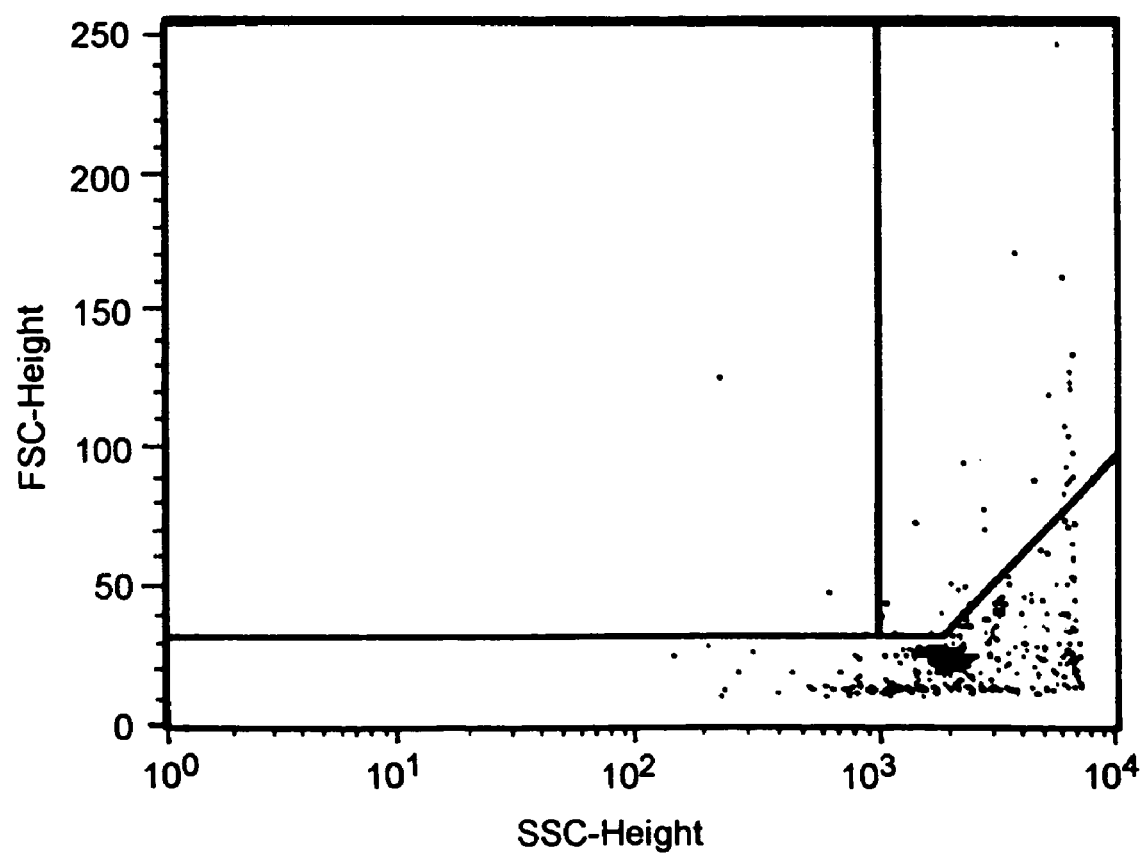
Figure 3C:
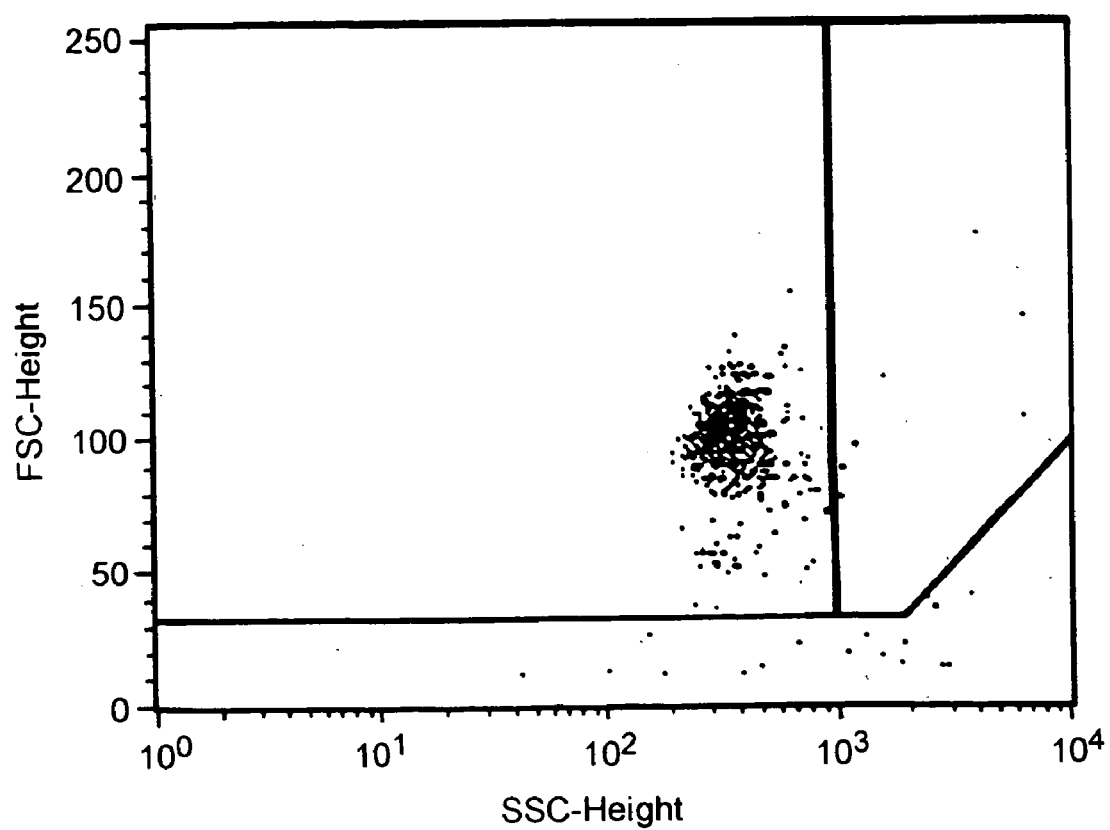
Figure 3D:
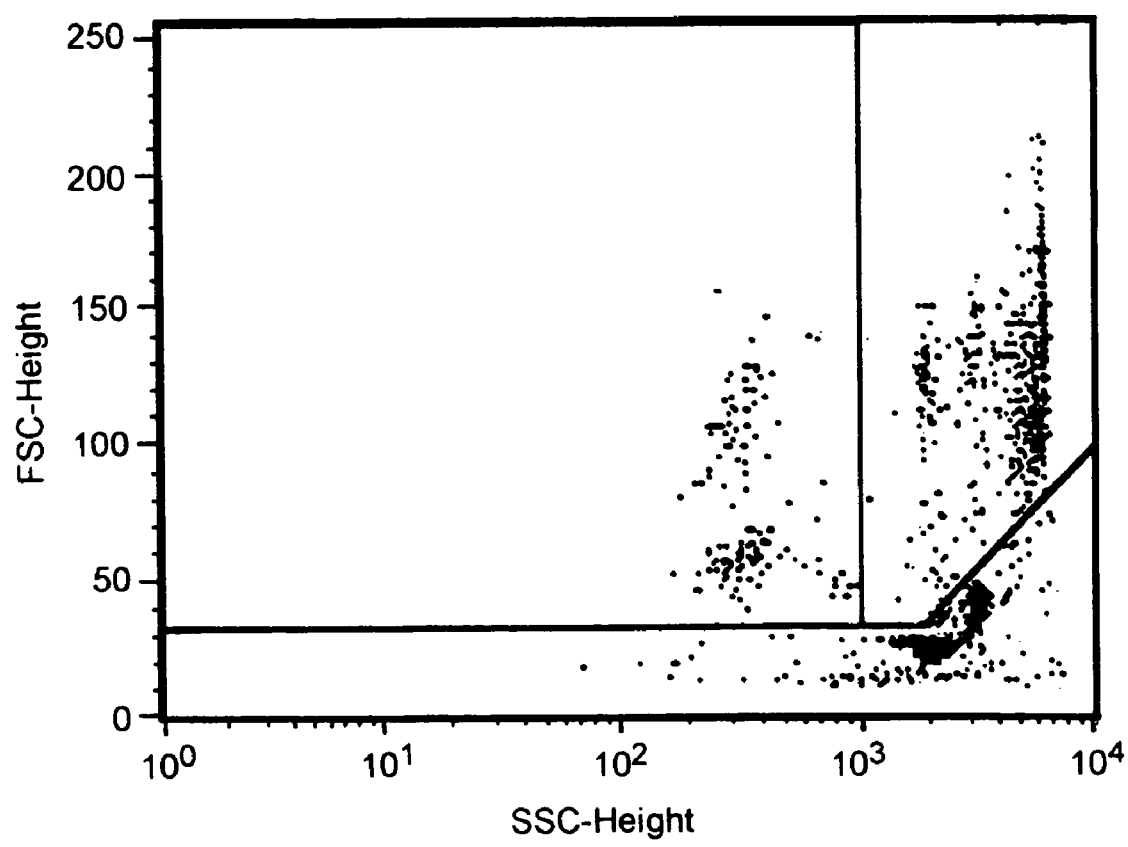
Figure 3E:
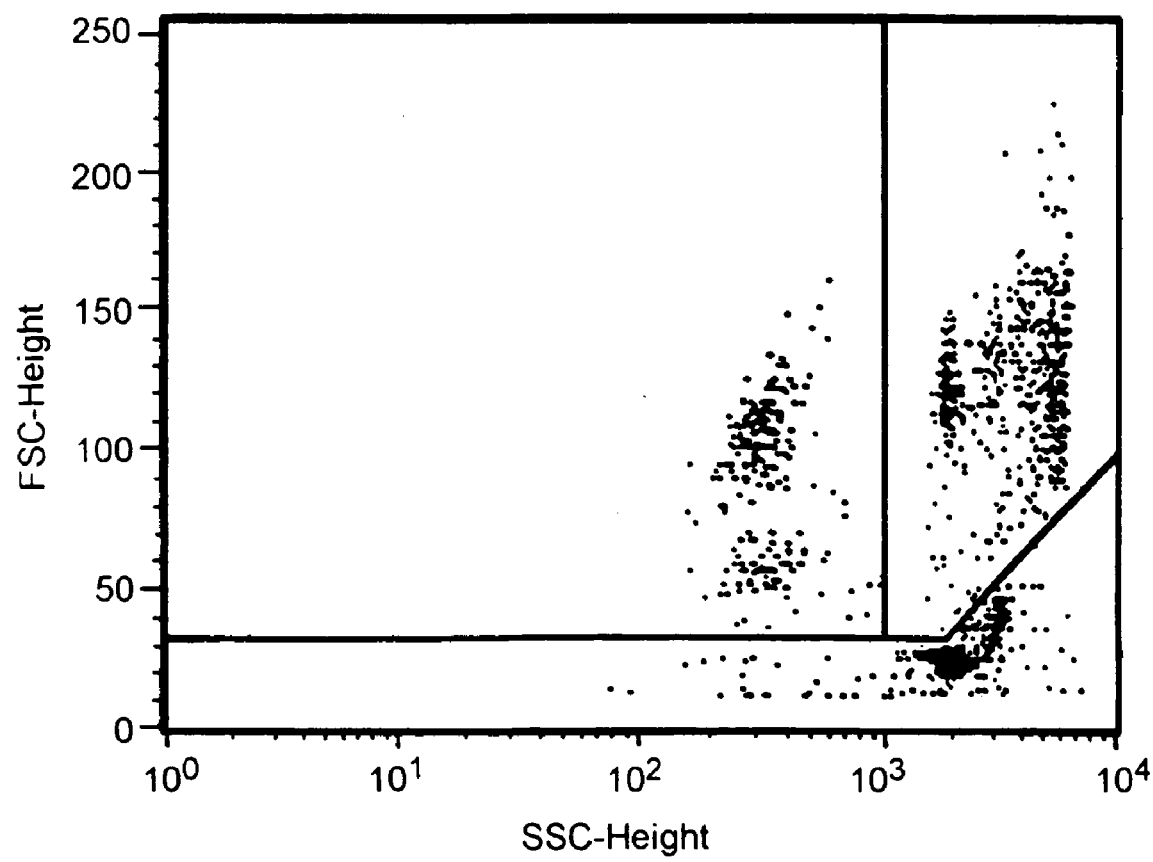
Figure 3F:
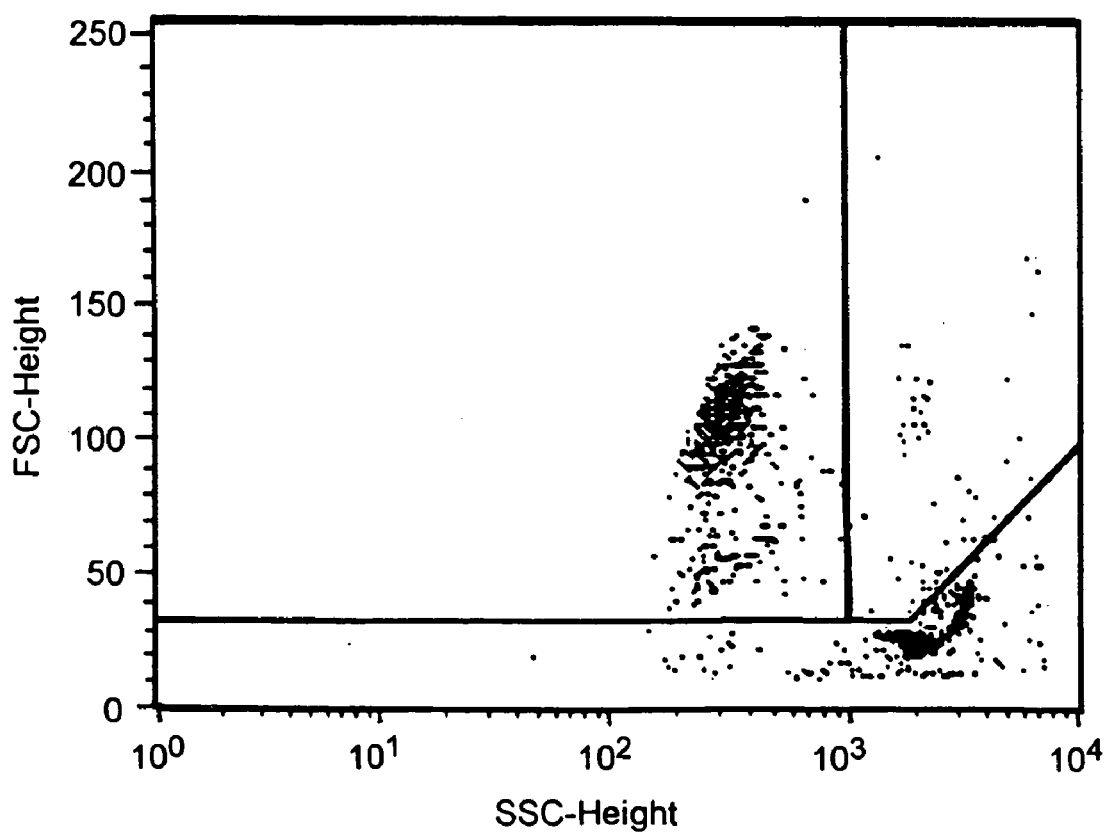
Figure 3G:
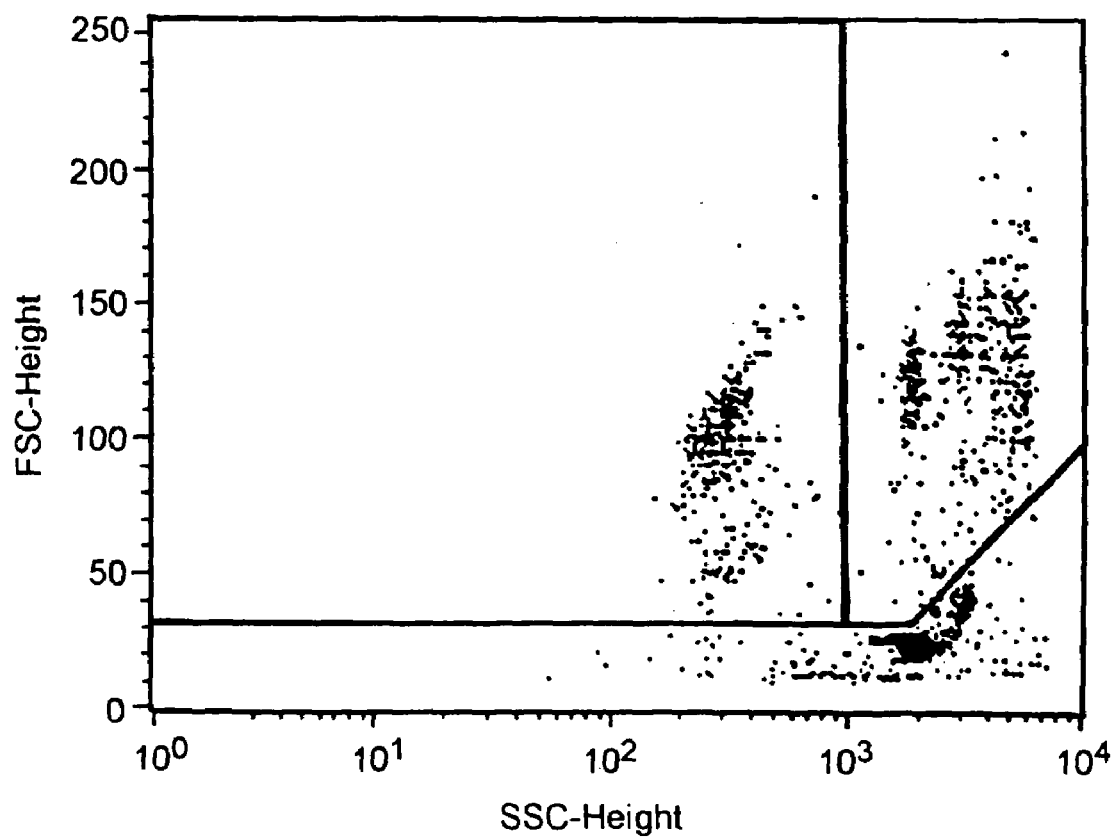
Figure 3H:
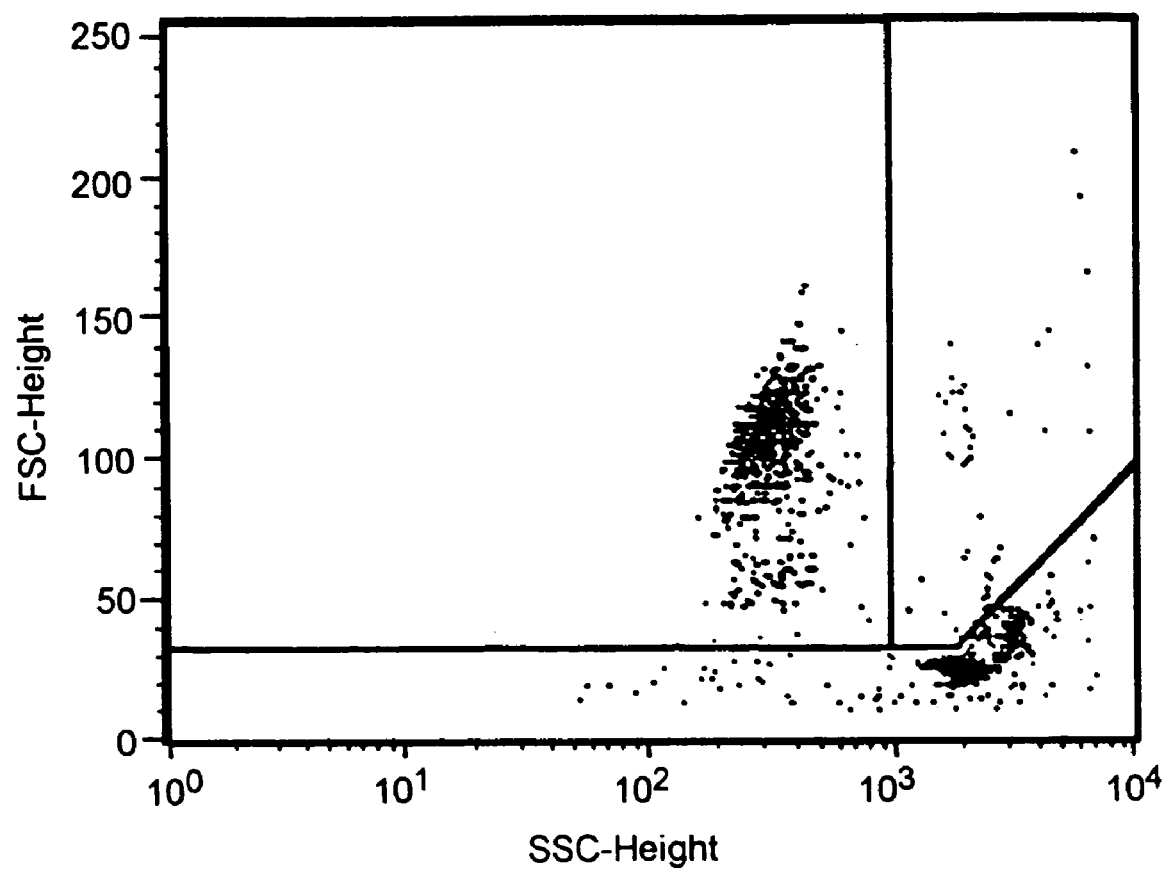

Adsorption was also quantitated by flow cytofluorometry using a FACSscan® (Becton Dickinson & Co., Mountain View, Calif.) by recording either green versus red fluorescence dot plots, or forward versus side scatter dot plots. To assess cell-bead complex formation using green versus red fluorescence dot plots, the beads were labeled in red with phycoerythrin (FIG. 2A: beads alone) and the cells were labeled in green with NHS-fluorescein (Pierce, Rockford, Ill.) (FIG. 2B: cells alone). Cell-bead complex formation was assessed by the appearance of green (G) and red (R) events. The percentage of cells complexed to beads, was calculated as the ratio RG/G+RG, where G is the number of events in the lower right quadrant and RG is the number of events in the upper right quadrant. We found that on such green versus red fluorescence dot plots (FIG. 2), cell-bead complex formation was quite apparent in the presence of antigenic peptides QL9 (FIG. 2C), p2Ca (FIG. 2D) and SL9 (FIG. 2E), with over 85% of the cells shifting to a high red fluorescence value. Some red and green colored events (2.2%) were detected in the sample incubated with a control peptide (LCMV) (FIG. 2F). This was most likely due to non-specific adsorption of a small amount of fluorescein-labeled cell debris to the beads.

Side scatter versus forward scatter dot plots were also usable for this quantitation, thanks to the fact that the cells (FIG. 3C) and the beads (FIG. 3B) had very different side and forward scatters, which made it easy to draw clearly distinct regions (FIG. 3A) containing the populations of events representing cells and beads respectively. Appearance of an additional population of events with a higher forward scatter than the beads and a higher side scatter than the cells, reflected cell-bead complex formation; this allowed to define complex region, distinct from the cell and bead regions. The percentage of cells adsorbed to beads was calculated as the ratio CO/CO+CE, where CO was the number of events in the complex region and CE was the number of events in the cell region. Such forward versus side scatter measurements showed antigen-specific adsorption of the 2C T cells to the beads: in the experiment shown in FIG. 3, 91.0% and 78.9% of the cells were adsorbed to $L^d$-coated beads in the presence of QL9 (FIG. 3D) and p2Ca (FIG. 3E) respectively and 63.8% of the cells were adsorbed to $K^{bm3}$-coated beads in the presence of dEV-8 (FIG. 3G) and 75.7% of the cells were adsorbed to $K^b$-coated beads in the presence of SIYR (not shown) after 4 hours of incubation. Several populations, which differed by their side scatter values, were visible in the complex region; they were likely to represent complexes containing different numbers of beads. In the presence of non-2C reactive $L^d$-LCMV (FIG. 3F), $K^{bm3}$-E1 (FIG. 3H) and $K^b$-E1 complexes, respectively 2.6%, 1.1% and 0.2% of events were found in the complex region.

We used flow cytofluorometry analysis to quantitate the influence of various parameters on cell-bead complex formation. Attachment of cells to beads was time dependent. Binding was detectable after 5 min of incubation, increased subsequently to reach a plateau between 1 and 4 hours, and decreased notably after 6 hours (FIG. 4A). Kinetics of adsorption were remarkably parallel for various peptide-MHC complexes. Attachment was also temperature dependent, as shown in FIG. 4B. At 4° C., only a small percentage of cells was captured on beads, even after prolonged incubation. Adsorption at room temperature was very similar to adsorption at 37° C. with the exception of $L^d$-p2Ca, for which attachment levels at 37° C. were about 25% of the values measured at room temperature, consistent with the inability of p2Ca to stabilize $L^d$ at 37° C. (Cai and Sprent, 1996). Finally, CD8 dependence of cell capture varied with the peptide-MHC complex: for instance, $L^d$-QL9 and $K^{bm3}$-SIYR captures were largely CD8 independent, whereas $L^d$-p2Ca and $K^{bm3}$-dEV-8 exhibited CD8 dependence (FIG. 4C).

EXAMPLE 3

Recovery of Antigen-specific T Cells Mixed with Irrelevant T Cells

T cell precursor frequencies in a naive animal are typically low. Magnetic beads have been found suitable in other systems to enrich low frequency cell populations (Sawada et al., 1990; Kato and Radbruch, 1993). To assess whether MHC class I-coated magnetic beads could be used for T cell precursor enrichment, we mixed fluorescein-labeled 2C T cells with CD8$^+$ T cells purified from naive C57BL/6 mice. After incubation with MHC-coated magnetic beads in the presence of peptide, adsorbed cells were eluted and counted, and the percentage of 2C T cells was determined by flow cytofluorometry. In the experiment shown in FIG. 5, 2C T cells were undetectable at the initial frequency of 0.03%. Following adsorption using $K^{bm3}$-coated beads and dEV-8 peptide, a definite peak of green fluorescence was observed, displaying the same intensity as the original fluorescein-stained 2C T cell population. This peak represented 65.1% of the eluted cells. No peak was observed when a control peptide was used instead of dEV-8. We achieved 800–1600 fold enrichment in 2C T cells in comparable experiments using beads coated with 3 different MHC-peptide complexes (table II). In all cases, the non-fluorescent cells in the eluted population represented only a minor fraction of the initial cell population (~0.2%).

EXAMPLE 4

In Vitro Isolation and Expansion of Antigen-specific CTL from Naive Mice

In Vitro Cell-mediated Cytotoxicity $L^d$-expressing RMA.S cells, EL4 cells (H-2$^b$), MC57 cells (H-2$^b$) infected with LCMV Armstrong (48 h.; multiplicity of infection: 1 PFU per cell) or BALB/c CL-7 cells (H-2$^d$) infected with LCMV Armstrong (48 h.; multiplicity of infection: 1 PFU per cell) were used as target cells. Target cells were loaded with 100 µCi of Na$_2$$^{51}$CrO$_4$ (New England Nuclear, Wilmington, Del.) per 10$^6$ cells at 37° C. for 60 min, in the presence of 20% FCS. They were washed three times and aliquoted in 96 well plates at 4,000 to 10,000 cells per well. Peptides and effector cells were then added. Final volume was 200 µl/well. Plates were incubated at 37° C. for 5 hours. One hundred µl of supernatant were collected and counted in a gamma counter. Percent specific lysis was calculated as previously reported (Wunderlich and Shearer, 1991).

In Vivo Assay for CTL Activity

Recipient mice were injected on day 0 with 2×10$^3$ PFU of LCMV Armstrong i.v. and adoptively transferred i.v. with cells on day 1. On day 2, mice were sacrificed, and the spleens were assayed for infectious virus titers by plaque assay on Vero cells as described previously (Byrne and Oldstone, 1984). Virus titers were expressed as plaque forming units per gram of tissue (pfu/g).

Cell Culture

Cells adsorbed onto beads were recovered by washing the beads 3 times with DMEM containing 10% FCS, and then cultured in 96 well plates coated with the appropriate MHC class I molecule and anti-CD28 antibody in the presence of 10 µM peptide; these conditions are sufficient to activate resting 2C T cells. Flat bottom well plates were used to ensure that every cell be in contact with the immobilized stimulatory molecules. After 2 days of culture at 37° C. under humid atmosphere containing 8% CO$_2$, half the volume of medium was replaced by fresh medium containing 20% of culture supernatant from concanavalin A-activated rat splenocytes (conA supernatant). After 8–12 days, cells were restimulated with spleen cells pulsed with 1 µM peptide, and cultured in the presence of 10% cona supernatant and 2 ng/ml of TGFβ$_1$ (Lee and Rich, 1991; Zhang et al, 1995).

Figure 6A:
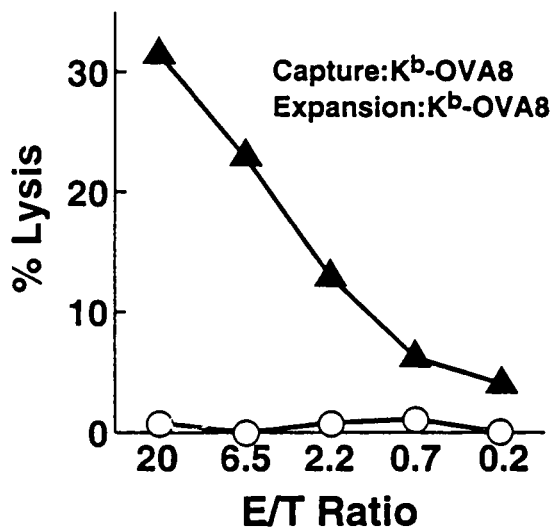
Figure 6B:
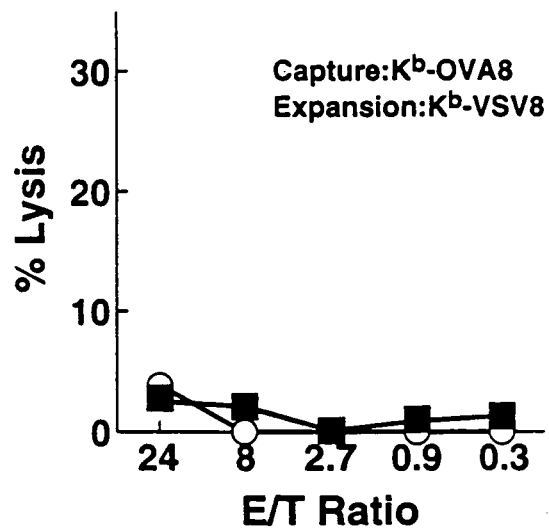
Figure 6C:
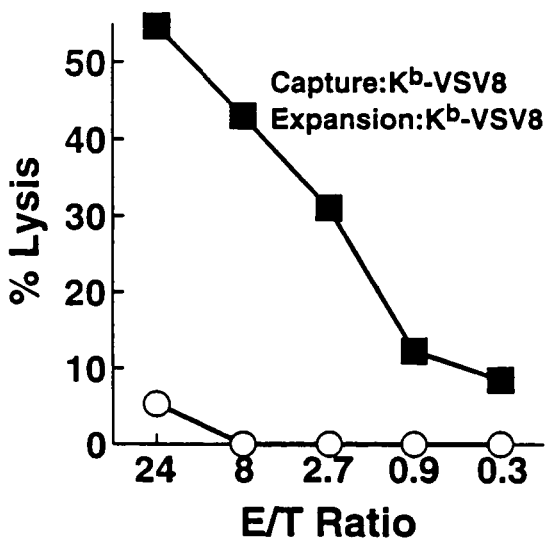
Figure 6D:
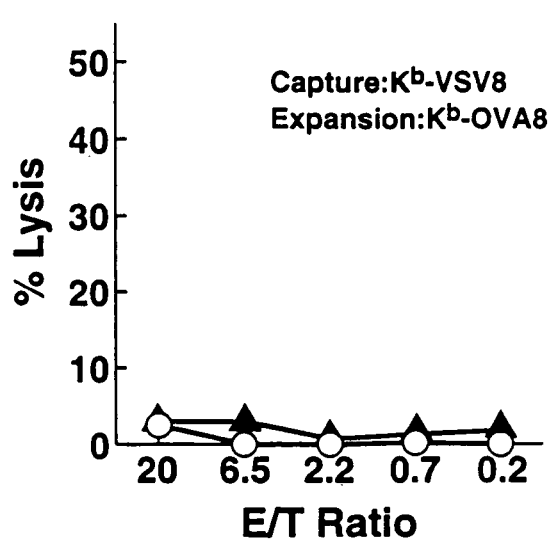

Generation of Antigen-specific CTL Lines from Naïve Mouse T Cells Using Adsorption on MHC-coated Magnetic Beads; Antigen Specificity of the Isolation Step To investigate whether the capture method would be applicable to isolate antigen-specific T cells from a naive animal, we incubated two aliquots of CD8$^+$ T cells purified from C57BL/6 mouse (H-$2^b$ haplotype) lymph nodes with $K^b$-coated magnetic beads in the presence of either OVA-8 peptide (aliquot 1) or VSV-8 peptide (aliquot 2) during 4 hours at room temperature. After 3 washes, cells were put in culture in 12 wells of a 96 well plate coated with $K^b$ and anti-CD28 mAb, in the presence of 10 μM of OVA-8 or VSV-8 peptide. Cultures were processed as indicated in the previous paragraph. Cell growth was visible after 7 days in wells containing adsorbed cells. Cells were restimulated on feeder cells at day 9, and tested for cytotoxic activity at day 18. Cells from aliquot 1 cultured with OVA-8 displayed a CTL activity specific for OVA-8 peptide (FIG. 6A), and cells from aliquot 2 cultured with VSV-8 displayed a CTL activity specific for VSV-8 (FIG. 6C). Controls were provided by the reverse combination: cells captured using OVA-8 peptide contained no detectable anti-VSV-8 CTL precursors, since they did not generate anti-VSV-8 CTL when VSV-8 was used rather than OVA-8 to activate them in culture (FIG. 6B); similarly, cells captured using VSV-8 peptide contained no detectable anti-OVA-8 CTL precursors (FIG. 6D).

To obtain an estimate of the CTLp frequencies after enrichment, we repeated the enrichment experiment using $K^b$-coated beads and OVA-8 peptide. In a representative experiment, the 12,000 cells that were recovered by adsorption to $K^b$-OVA8-coated magnetic beads were aliquoted and cultured separately in 12 wells of 96 well plates immediately after capture. Specific CTL were recovered from cultured captured cells in 3 wells, indicating that the precursor frequency after capture was approximately 1/3,500. Similar results were obtained in three independent experiments.

Figure 7A:
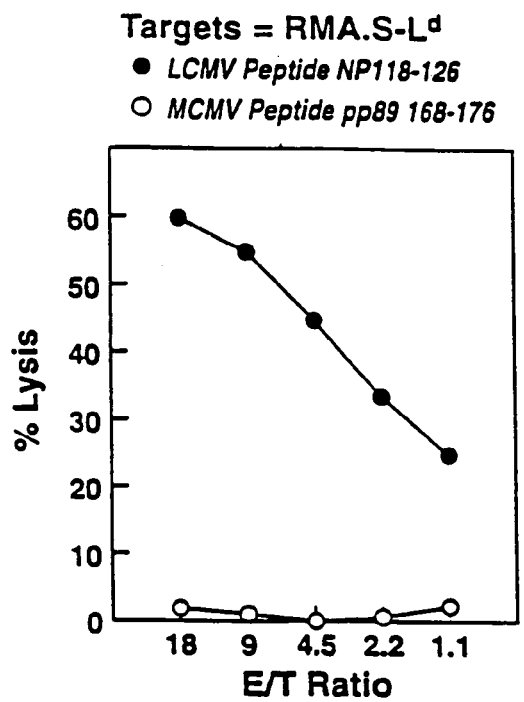
Figure 7B:
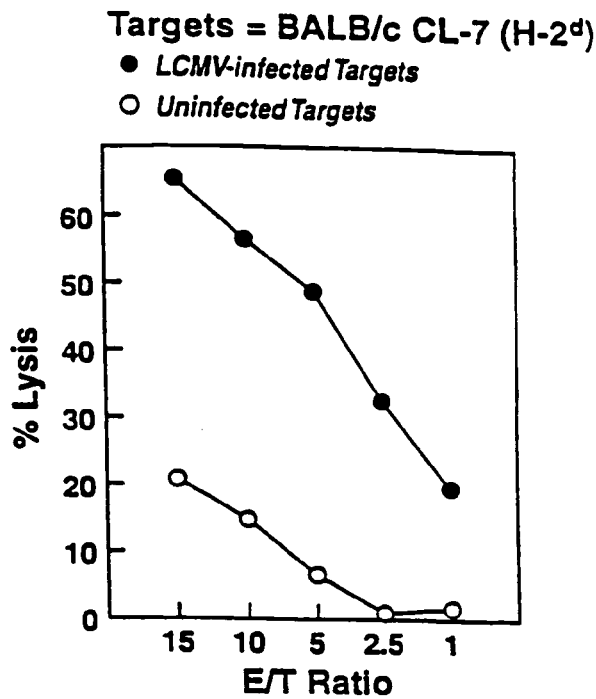
Figure 7C:
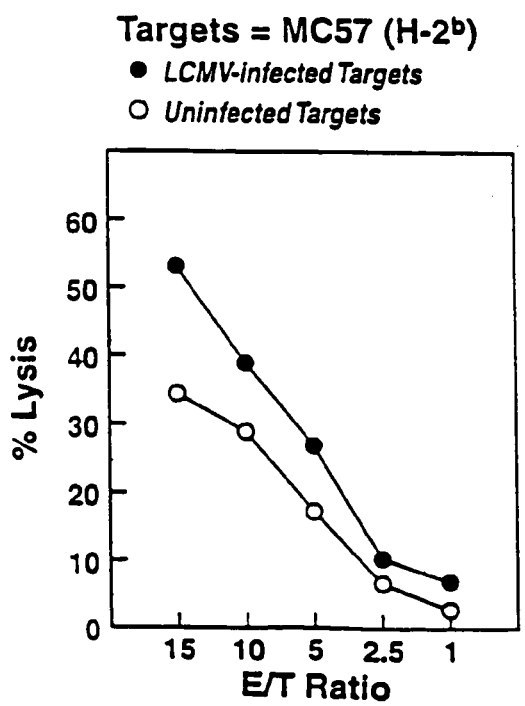
Figure 7D:
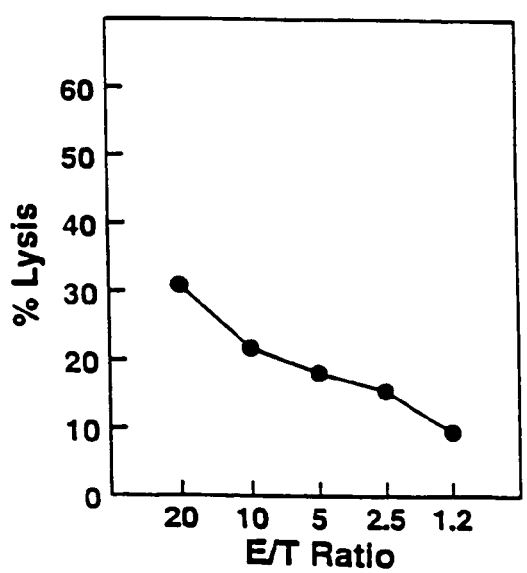

Generation of Anti-LCMV CTL from Naïve Mouse T Cells; In Vitro and In Vivo Anti-viral Activity We derived anti-LCMV CTL by incubating $10^7$ CD8$^+$ T cells purified from BALB/c mouse (H-$2^d$ haplotype) lymph nodes together with $L^d$-coated magnetic beads in the presence of LCMV peptide during 4 hours at room temperature. After 3 washes, about $10^4$ cells were recovered and put in culture in 12 wells of a 96 well plate coated with $L^d$ and anti-CD28 mAb, in the presence of 10 μM of LCMV peptide. Cells were cultured as indicated in the previous paragraph. As shown in FIG. 7A, we obtained cytotoxic T lymphocytes (CTL) specific for LCMV peptide. Cells also killed LCMV-infected targets of the H-$2^d$ haplotype, while displaying only a background activity against uninfected targets (FIG. 7B). An anti-allotypic activity (FIG. 7C) as well as some NK/LAK activity were also present (FIG. 7D). All cells expressed CD8, as judged by flow cytofluorometry. In vivo assay showed that the cells were able to markedly reduce virus titers in BALB/c mice (H-$2^d$) acutely infected with LCMV (FIG. 8). This reduction was MHC-specific since no significant reduction of the virus titers were observed in C57/BL6 mice (H-$2^b$) following CTL injection.

BIBLIOGRAPHICAL REFERENCES

Agrawal G B, Linderman J J (1996) Mathematical modeling of helper T lymphocyte/antigen-presenting cell interactions: analysis of methods for modifying antigen processing and presentation. J. Theor. Biol. 182, 487–504.

Ashman R F (1973) Lymphocyte receptor movement induced by sheep erythrocyte binding. J. Immunol. 111, 212–220.

Altman J D, Moss P A H, Goulder J P R, Barouch D H, McHeyzer-Williams M G, Bell J I, McMichael A J, Davis M M (1996) Phenotypic analysis of antigen-specific T lymphocytes. Science 274, 94–96.

Bellone G, Geuna M, Carbone A, Silvestri S, Foa R, Emanuelli G, Matera L (1995) Regulatory action of prolactin on the in vitro growth of CD34$^+$ve human hemopoietic progenitor cells. J. Cell. Physiol. 163, 221–231.

Borrow P, Oldstone M B A (1997) Lymphocytic choriomeningitis virus. In: "Viral Pathogenesis", Neal Nathanson et al., ed. Lippincott-Raven Publishers, Philadelphia, pp. 593–627.

Cai Z, Sprent J (1996) Influence of antigen dose and costimulation on the primary response of CD8$^+$ I cells in vitro. J. Exp. Med. 183, 2247–2257.

Cai Z, Brunmark A, Jackson M R, Loh D, Peterson P A, Sprent J (1996) Transfected Drosophila cells as a probe for defining the minimal requirements for stimulating unprimed CD8$^+$ T cells. Proc. Natl. Acad. Sci. USA 93, 14736–14741.

Corr M, Slanetz A E, Boyd L F, Jelonek M T, Khilko S, Al-Ramadi B K, Sang Kim Y, Maher S E, Bothwell A L M, Margulies D H (1994) T cell receptor-MHC class I peptide interactions: affinity, kinetics, and specificity. Science 265, 946–949.

De Bruijn M L H, Nieland J D, Schumacher T N M, Ploegh H L, Kast W M, Melief C J M (1992) Mechanisms of induction of primary virus-specific cytotoxic T lymphocyte responses. Eur. J. Immunol. 22, 3013–3020.

Dillon S R, Jameson S C, Fink P J (1994) Vβ5$^+$ T cell receptors skew toward OVA+H-2K$^b$ recognition. J. Immunol. 152, 1790–1801.

Engelhard V H (1994) Structure of peptides associated with MHC class I molecules. Current Opinion Immunol. 6, 13–23.

Gold M R, DeFranco A L (1994) Biochemistry of B lymphocyte activation. Adv. Immunol. 55, 221–295.

Grupp S A, Snow E C, Harmony J A K (1987) The phosphatidylinositol response is an early event in the physiologically relevant activation of antigen-specific B lymphocytes. Cell. Immunol. 109, 181–191.

Hou S, Hyland L, Ryan K W, Portner A, Doherty, P C (1994) Virus-specific CD8$^+$ T-cell memory determined by clonal burst size. Nature 369, 652–654.

Irsch J, Irlenbusch S, Radl J, Burrows P D, Cooper M D, Radbruch A H (1994) Switch recombination in normal IgA$_1^+$ B lymphocytes. Proc. Natl. Acad. Sci. USA 91, 1323–1327.

Jackson M R, Song E S, Yang Y, Peterson P A (1992) Empty and peptide-containing conformers of class I major histocompatibility complex molecules expressed in Drosophila melanogaster cells Proc. Natl. Acad. Sci. USA 89, 12117–12121.

Kane K P, Goldstein S A N, Mescher M F (1988) Class I alloantigen is sufficient for cytolytic T lymphocyte binding and transmembrane signaling. Eur. J. Immunol. 18, 1925–1929.

Kane K P, Mescher M F (1993) Activation of CD8-dependent cytotoxic T lymphocyte adhesion and degranulation by peptide class I antigen complexes. J. Immunol. 150, 4788–4797.

Kato K, Radbruch A (1993) Isolation and characterization of CD34$^+$ hematopoietic stem cells from human peripheral blood by high-gradient magnetic cell sorting. Cytometry 14, 384–392.

Klavinskis L S, Tishon A, Oldstone M B A (1989) Efficiency and effectiveness of cloned virus-specific cytotoxic T lymphocytes in vivo. J. Immunol. 143, 2013–2016.

Kranz D M, Tonegawa S, Eisen H N (1994) Attachment of an anti-receptor antibody to non-target cells renders them susceptible to lysis by a clone of cytotoxic T lymphocytes. Proc. Natl. Acad. Sci. USA 81, 7922–7926.

Lau L L, Jamieson B D, Somasundaram T, Ahmed R (1994) Cytotoxic T-cell memory without antigen. Nature 369, 648–652.

Lee H, Rich S (1991) Co-stimulation of T cell proliferation by transforming growth factor-β1. J. Immunol. 147, 2991–3000.

Luxembourg A T, Cooper N R (1994) Modulation of signaling via the B cell antigen receptor by CD21, the receptor for C3dg and EBV. J. Immunol. 153, 4448–4467.

Matsui K, Jay Boniface J, Reay P A, Schild H, Fazekas de St. Groth B, Davis M M (1991) Low affinity interaction of peptide-MHC complexes with T cell receptors. Science 254, 1788–1791.

Mescher M F (1995) Molecular interactions in the activation of effector and precursor cytotoxic T lymphocytes. Immunol. Rev. 146, 177–210.

Moore M D, DiScipio R G, Cooper N R, Nemerow G R (1989) Hydrodynamic, electron microscopic, and ligand-binding analysis of the Epstein-Barr virus/C3dg receptor (CR2). J. Biol. Chem. 264, 20576–20582.

Myers C D, Kriz M K, Sullivan T J, Vitettta E S (1987)) Antigen-induced changes in phospholipid metabolism in antigen-binding B lymphocytes. J. Immunol. 138, 1705–1711.

Nakanishi M, Brian A A, McConnell H M (1983) Binding of cytotoxic T-lymphocytes to supported lipid monolayers containing trypsinized H-2K$^k$. Mol. Immunol. 20, 1227–1231.

Noelle R J, Snow E C (1990) Cognate interactions between helper T cells and B cells. Immunol. Today 11, 361–368.

Oehen S, Waldner H, Kündig T M, Hengartner H, Zinkernagel R M (1992) Antivirally protective cytotoxic T cell memory to lymphocytic choriomeningitis virus is governed by persisting antigen. J. Exp. Med. 176, 1273–1281.

Radbruch A, Recktenwald D (1995) Detection and isolation of rare cells. Curr. Opin. Immunol. 7, 270–273.

Ramensee H G, Friede T, Stevanovic S (1995) MHC ligands and peptide motifs: first listing. Immunogenetics 41, 178–228.

Sawada K, Krantz S B, Dai C H, Koury S T, Horn S T, Glick A D, Civin C I (1990) Purification of human blood burst-forming units-erythroid and demonstration of the evolution of erythropoietin receptors. J. Cell. Physiol. 142, 219–230.

Sha W C, Nelson C A, Newberry R D, Kranz D M, Russell J H, Loh D Y (1988) Selective expression of an antigen receptor on CD8-bearing T lymphocytes in transgenic mice. Nature 335, 271–274.

Snow E C, Vitetta E S, Uhr J W (1983a) Activation of antigen-enriched B cells. I. Purification and response to thymus-independent antigens. J. Immunol. 130, 607–613.

Snow E C, Noelle R J, Uhr J W, Vitetta E S (1983b) Activation of antigen-enriched B cells. II. Role of linked recognition in B cell proliferation to thymus-dependent antigens. J. Immunol. 130, 614–618.

Snow E C, Fetherson J D, Zimmer S (1986) Induction of the c-myc protooncogene after antigen binding to hapten-specific B cells. J. Exp. Med. 164, 944–949.

Stein P, Dubois P, Greenblatt D, Howard M (1986) Induction of antigen-specific proliferation in affinity-purified small lymphocytes: requirement for BSF-1 by type 2 but not type 1 thymus-independent antigens. J. Immunol. 136, 2080–2089.

Sun S, Cai Z, Langlade-Demoyen P, Brunmark A, Jackson M R, Peterson P A, Sprent J (1996) Dual function of Drosophila cells as APCs for naive CD8$^+$ T cells: implications for tumor immunotherapy. Immunity 4, 555–564.

Sykulev Y, Brunmark A, Jackson M, Cohen R J, Peterson P A, Eisen H N (1994a) Kinetics and affinity of reactions between an antigen-specific T cell receptor and peptide-MHC complexes. Immunity 1, 15–22.

Sykulev Y, Brunmark A, Tsomides T J, Kageyama S, Jackson M, Peterson P A, Eisen H N (1994b) High-affinity reactions between antigen-specific T-cell receptors and peptides associated with allogeneic and syngeneic major histocompatibility complex class I proteins. Proc. Natl. Acad. Sci. USA 91, 11487–11491.

Tallquist M D, Pease L R (1995) Alloreactive 2C T cells recognize a self peptide in the context of the mutant K$^{bm3}$ molecule. J. Immunol. 155, 2419–2426.

Tallquist M D, Yun T J, Pease L R (1996) A single T cell receptor recognizes structurally distinct MHC/peptide complexes with high specificity. J. Exp. Med. 184, 1017–1026.

Ukada K, Wiesmüller K H, Kienle S, Jung G, Walden P (1996) Self-MHC-restricted peptides recognized by an alloreactive T lymphocyte clone. J. Immunol. 157, 670–678.

Weber S, Traunecker A, Oliveri F, Gerhard W, Kaijalainen K (1992) Specific low-affinity recognition of major histocompatibility complex plus peptide by soluble T-cell receptor. Nature 356, 793–796.

Wilson H A, Greenblatt D, Poenie M, Finkelman F D, Tsien R Y (1987) Crosslinkage of B lymphocyte surface immunoglobulin by anti-Ig or antigen induces prolonged oscillation of intracellular ionized calcium. J. Exp. Med. 166, 601–606.

Wunderlich J, Shearer G (1991) Induction and measurement of cytotoxic T lymphocyte activity. In: "Current Protocols in Immunology" (Coligan J E, Kruisbeek A M, Margulies D H, Shevach E M, Strober W, eds.) John Wiley and Sons, New York, pp. 3.11.1–3.11.15.

Zhang X, Giangreco L, Broome H E, Dargan C M, Swain S L (1995) Control of CD4 effector fate: transforming growth factor β1 and interleukin 2 synergize to prevent apoptosis and promote effector expansion. J. Exp. Med. 182, 699–709.

TABLE I

Capture of 2C T cells on L$^d$-coated magnetic beads in the presence of various peptides as assessed by microscopic examination

| Peptide | % Cell captured | 2C TCR affinity for L$^d$-peptide (M$^{-1}$) | Peptide affinity for L$^d$ (M$^{-1}$) |
| --- | --- | --- | --- |
| QL9 | 87% | $10^7$ | $2 \times 10^8$ |
| p2Ca | 83% | $2 \times 10^6$ | $4 \times 10^6$ |
| SL9 | 77% | $1.4 \times 10^4$ | $4 \times 10^7$ |
| MCMV | <1% | $<10^3$ | $2 \times 10^9$ |

TABLE II

Recovery of 2C T cells mixed with CD8+ T cells
from naive B6 mouse by adsorption
on MHC class I-coated magnetic beads

| MHC molecule | Peptide | % 2C T cell before enrichment | % 2C T cell after enrichment | 2C T cell enrichment | 2C T cell recovery | Number of experiments |
|---|---|---|---|---|---|---|
| $L^d$ | QL9 | 0.03% | 24.8 ± 6.9% | 828 ± 230 fold | 90.0 ± 14.0% | 3 |
| $K^{bm3}$ | dEV-8 | 0.03% | 50.9 ± 14.2% | 1697 ± 473 fold | 47.7 ± 1.7% | 2 |
| $K^b$ | SIYR | 0.03% | 47.6 ± 2.1% | 1588 ± 71 fold | 56.8 ± 0.6% | 2 |

What is claimed is:

1. A substrate for capturing antigens, comprising a support having on its surface a population of purified immobilized empty MHC Class I molecules, wherein said MHC Class I molecules are $K^{bm3}$ or $L^D$ molecules expressed from a recombinant *Drosophila* cell and are capable of binding one or more antigens, and wherein said substrate is not a lipid bilayer.

2. The substrate of claim 1 wherein the substrate is a bead.

3. The substrate of claim 1 wherein the one or more antigens are peptides.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (iv) ANTI-SENSE: NO (xi) SEQUENCE DESCRIPTION: SEQ ID NO: 1:

Gln Leu Ser Pro Phe Pro Phe Asp Leu
1             5

(2) INFORMATION FOR SEQ ID NO: 2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iv) ANTI-SENSE: NO (xi) SEQUENCE DESCRIPTION: SEQ ID NO: 2:

Leu Ser Pro Phe Pro Phe Asp Leu
1             5

(2) INFORMATION FOR SEQ ID NO: 3:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (iv) ANTI-SENSE: NO (xi) SEQUENCE DESCRIPTION: SEQ ID NO: 3:

Ser Pro Phe Pro Phe Asp Leu Leu Leu
1             5

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO: 4:

Leu Ser Ala Phe Pro Phe Asp Leu
1               5

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO: 5:

Glu Gln Tyr Lys Phe Tyr Ser Val
1               5

(2) INFORMATION FOR SEQ ID NO: 6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO: 6:

Ser Ile Tyr Arg Tyr Tyr Gly Leu
1               5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO: 7:

Arg Pro Gln Ala Ser Gly Val Tyr Met
1               5

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: single
        (D) TOPOLOGY: linear

```
        (ii) MOLECULE TYPE: peptide (iv) ANTI-SENSE: NO (xi) SEQUENCE DESCRIPTION: SEQ ID NO: 8:

Tyr Pro His Phe Met Pro Thr Asn Leu
1               5

(2) INFORMATION FOR SEQ ID NO: 9:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO: 9:

Ser Ile Ile Asn Phe Glu Lys Leu
1               5

(2) INFORMATION FOR SEQ ID NO: 10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO: 10:

Arg Gly Tyr Val Tyr Gln Gly Asn
1               5

(2) INFORMATION FOR SEQ ID NO: 11:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iv) ANTI-SENSE: NO (xi) SEQUENCE DESCRIPTION: SEQ ID NO: 11:

Glu Ile Ile Asn Phe Glu Lys Leu
1               5
```